United States Patent [19]

Higley et al.

[11] Patent Number: 5,290,801

[45] Date of Patent: Mar. 1, 1994

[54] BENZIMIDAZOLES FOR THE TREATMENT OF ATHEROSCLEROSIS

[75] Inventors: C. Anne Higley, Newark; Thomas P. Muduskuie, Jr.; Ruth R. Wexler, both of Wilmington; Richard G. Wilde, New Castle, all of Del.

[73] Assignee: The Du Pont Merck Pharmaceutical Company, Wilmington, Del.

[21] Appl. No.: 889,909

[22] Filed: May 29, 1992

[51] Int. Cl.$^5$ ............................................. A61K 31/415
[52] U.S. Cl. ..................................... 514/395; 514/394
[58] Field of Search ..................... 548/307.1; 514/394, 514/395

[56] References Cited

U.S. PATENT DOCUMENTS 3,718,662  2/1973  Venkatachala et al. ......... 548/307.1
4,814,329  3/1989  Harsányi et al. .................. 548/307.1
5,179,115  1/1993  Bruneau et al. ..................... 514/387

Primary Examiner—Mary C. Lee
Assistant Examiner—Mary Susan H. Gabilan
Attorney, Agent, or Firm—Gildo E. Fato

[57] ABSTRACT

This invention relates to imidazoles, namely, fused-ring heterocycles as inhibitors of acyl-CoA: cholesterol acyltransferase (ACAT), pharmaceutical compositions containing them, processes for their preparation, and their use as antihypercholesterolemic and/or antiatherosclerotic agents for the treatment of atherosclerosis.

8 Claims, No Drawings

BENZIMIDAZOLES FOR THE TREATMENT OF ATHEROSCLEROSIS

FIELD OF THE INVENTION

This invention relates to imidazoles as inhibitors of acyl-CoA: cholesterol acyltransferase (ACAT), pharmaceutical compositions containing them, processes for their preparation, and their use as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There is an increasing number of patents in the literature disclosing compounds which are useful as ACAT inhibitors in particular and antiatherosclerotic agents in general. For example, U.S. Pat. No. 4,623,662, issued to De Vries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol.

U.S. Pat. No. 4,868,210, issued to Trivedi on Sep. 19, 1989, as well as U.S. Pat. No. 4,923,896, May 8, 1990, disclose certain N-2,6-dialkyl- or N-2,6-dialkoxyphenyl-N'-arylalkyl ureas as potent inhibitors of ACAT.

European Patent Application 354,994, filed by Meguro and Ikeda which published on Feb. 21,1990, discloses certain N-aryl-N'-quinolin-4-yl ureas as ACAT inhibitors. European Patent Application 370,740, filed by Jackson et al. which published on May 30, 1990, discloses ACAT inhibitors similar in composition to those of deVries (vide supra) but different in constitution.

Billheimer, et al., European Patent Application EP-A-372,445, published on Jun. 13, 1990, discloses compounds of the formula:

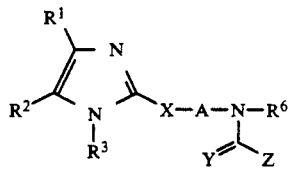

wherein
R$^1$ and R$^2$ are selected independently from H, C$_1$-C$_8$ alkyl, C$_3$-C$_8$ branched alkyl, C$_3$-C$_7$ cycloalkyl, C$_4$-C$_{10}$ cycloalkylalkyl, C$_7$-C$_{14}$ araalkyl, 2-, 3- or 4-pyridinyl, 2-thienyl, 2-furanyl, phenyl optionally substituted with 1 to 3 groups selected from F, Cl, Br, OH, C$_1$-C$_4$ alkoxy, C$_1$-C$_4$ alkyl, C$_3$-C$_8$ branched alkyl, CH$_3$S(O)$_r$, NO$_2$, CF$_3$ or NR$^7$R$^8$; or
R$^1$ and R$^2$ can also be taken together as

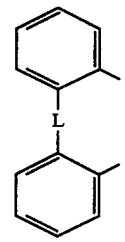

where L is O, O(CH$_2$)$_{m+1}$O or (CH$_2$)$_m$ where m is 0-4;
R$^3$ is H, C$_1$-C$_6$ alkyl, allyl, benzyl or phenyl optionally substituted with F, Cl, CH$_3$, CH$_3$O or CF$_3$;
R$^4$ is straight chain C$_1$-C$_8$ alkyl optionally substituted with F; C$_3$-C$_8$ branched alkyl, C$_3$-C$_7$ cycloalkyl, C$_4$-C$_{10}$ cycloalkylalkyl, C$_7$-C$_{14}$ araalkyl where the aryl group is optionally substituted with 1 to 3 groups selected from C$_1$-C$_4$ alkyl or alkoxy, F, Br, Cl, NH$_2$, OH, CN, CO$_2$H, CF$_3$, NO$_2$, C$_1$-C$_4$ carboalkoxy, NR$^7$R$^8$ or NCOR$^7$; C$_3$-C$_6$ alkenyl or alkynyl, C$_1$-C$_3$ perfluoroalkyl, phenyl optionally substituted with 1 to 3 groups selected from C$_1$-C$_4$ alkyl, C$_3$-C$_8$ branched alkyl, C$_1$-C$_4$ alkoxy, F, Br, Cl, NH$_2$, OH, CN, CO$_2$H, CF$_3$, NO$_2$, C$_1$-C$_4$ carboalkoxy, NR$^7$R$^8$ or NCOR$^7$; pentafluorophenyl, benzyl optionally substituted with 1 to 3 groups selected from C$_1$-C$_4$ alkyl or alkoxy, F, Br, Cl, NH$_2$, OH, CN, CO$_2$H, CF$_3$, NO$_2$, C$_1$-C$_4$ carboalkoxy, NR$^7$R$^8$ or NCOR$^7$; 2-, 3- or 4-pyridinyl, pyrimidinyl or biphenyl;
R$^5$ is H, C$_1$-C$_6$ alkyl or benzyl; R$^6$ is C$_1$-C$_8$ alkyl, C$_3$-C$_8$ branched alkyl, C$_3$-C$_7$ cycloalkyl, C$_3$-C$_8$ alkenyl or alkynyl, phenyl optionally substituted with 1 to 3 groups selected from C$_1$-C$_4$ alkyl or alkoxy, F, Br, Cl, NH$_2$, OH, CN, CO$_2$H, CF$_3$, NO$_2$, C$_1$-C$_4$ carboalkoxy, NR$^7$R$^8$ or NCOR$^7$; pentafluorophenyl, benzyl optionally substituted with 1 to 3 groups selected from C$_1$-C$_4$ alkyl or alkoxy, F, Br, Cl, NH$_2$, OH, CN, CO$_2$H, CF$_3$, NO$_2$, C$_1$-C$_4$ carboalkoxy, NR$^7$R$^8$ or NCOR$^7$;
R$^7$ and R$^8$ are selected independently from H or C$_1$-C$_4$ alkyl;
X is S(O)r, O, NR$^5$, CH$_2$;
A is C$_2$-C$_{10}$ alkyl, C$_3$-C$_{10}$ branched alkyl, C$_3$-C$_{10}$ alkenyl or C$_3$-C$_{10}$ alkynyl;
Y is O, S, H$_2$, NH;
Z is NHR$^4$, OR$^4$ or R$^4$;
r is 0-2, or a pharmaceutically acceptable salt thereof.

These compounds are potent in vitro inhibitors of ACAT and are therefore potential antihypercholesterolemic agents.

U.S. Pat. No. 4,900,744, issued to Billheimer et al. on Feb. 13, 1990, discloses antihypercholesterolemic thioimidazoles of the formula:

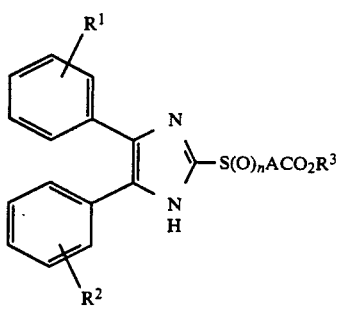

or a pharmaceutically acceptable salt thereof, wherein
R$^1$ and R$^2$ independently are H, F, Cl, CF$_3$, alkyl of to 4 carbon atoms or alkoxy of 1 to 4 carbon atoms;
A is alkylene of 7-20 carbon atoms of an alkenyl residue thereof with no more than 2 double bonds;
R$^3$ is H, CH$_3$, of C$_2$H$_5$; and
n is 0, 1 or 2, such as 8-(4,5-diphenyl-1H-imidazol-2-ylthio)octanoic acid ethyl ester.

U.S. Pat. No, 4,460,598, issued to Lautenschläger et al. on Jul. 17, 1984, discloses compounds of the formula:

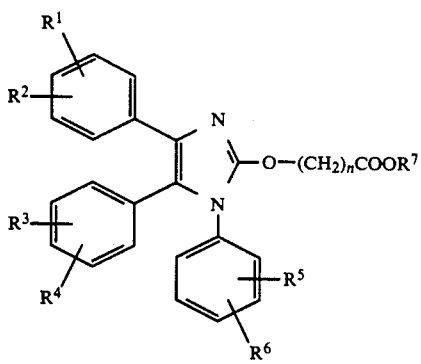

wherein
R$^1$, R$^2$, R$^3$, R$^4$, R$^5$ and R$^6$ independently are H, F, Cl, Br, I, alkyl, alkoxy or CF$_3$, with the proviso that one or several of R$^1$ and R$^2$, R$^3$ and R$^4$ or R$^5$ and R$^6$ taken together represent methylenedioxy;
R$^7$ is H, alkali metal ion, alkyl of 1 to 6 carbon atoms or benzyl; and
n is 0 to 10.

The synthesis and the use of these compounds in the treatment of thromboembolic, inflammatory and/or atherosclerotic diseases is disclosed.

U.S. Pat. No. 4,654,358, issued to Lautenschläger et al on Mar. 31, 1987, discloses compounds of the formula:

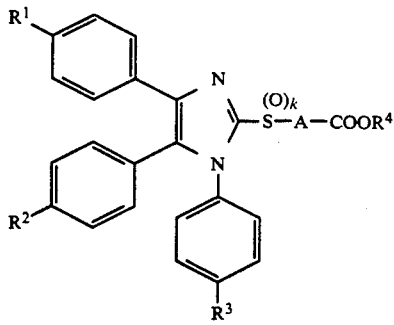

wherein
k is 0, 1 or 2,
R$^1$, R$^2$ and R$^3$ independently are H, F, Cl, CH$_3$, CH$_3$O or CF$_3$;
R$^4$ is H, Na, K, CH$_3$, CH$_3$CH$_2$, (CH$_3$)$_2$CH, CH$_3$(CH$_2$)$_2$ or butyl;
A is C(CH$_3$)$_2$, CH(CH$_2$)$_m$CH$_3$, (CH$_2$)n or (CH$_2$)$_{n-2}$CH(CH$_3$);
m is 0 to 8; and
n is 2 to 10.

The synthesis and the use of these compounds in the treatment of inflammatory diseases, diseases of lipid metabolism, and/or hyperlipidemic diseases is disclosed.

German Laid Open Application No. DE 3504679, Lautenschläger et al., published Aug. 14, 1986, discloses compounds of the formula:

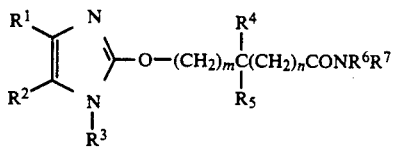

wherein
R$^1$, R$^2$ and R$^3$ independently are H, alkyl of 1 to 6 carbon atoms, cycloalkyl of 1 to 6 carbon atoms or

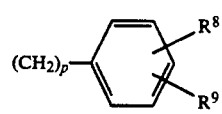

R$^4$ and R$^5$ independently are H, C$_6$H$_5$ or alkyl of 1 to carbon atoms;
R$^6$ and R$^7$ independently are H, OH, saturated or unsaturated alkyl, cycloalkyl or hydroxyalkyl of 1 to 10 carbon atoms,

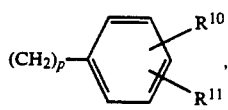

-continued

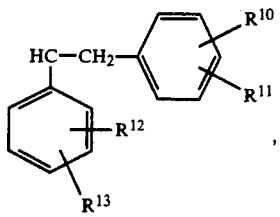

or

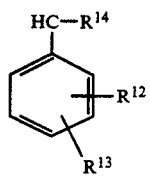

$R^8$, $R^9$, $R^{10}$, $R^{11}$, $R^{12}$ and $R^{13}$ independently are H, F, Cl, Br, $NO_2$, $CH_3CONH$, OH, alkyl of 1 to 3 carbon atoms, $CF_3$, and alkoxy of 1 to 3 carbon atoms, with the proviso that $R^8$ and $R^9$, $R^{10}$ and $R^{11}$ or $R^{12}$ and $R^{13}$ taken together represent methylenedioxy;

$R^{14}$ is alkyl of 1 to 2 carbon atoms;

m and n taken together represent a whole number from to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

German Laid Open Application No. DE 3504680, Lautenschläger et al., published Aug. 14, 1986, discloses compounds of the formula:

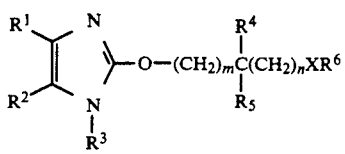

wherein $R^1$, $R^2$ and $R^3$ independently are H, alkyl of 1 to 6 carbon atoms, cycloalkyl of 1 to 6 carbon atoms or

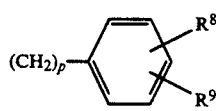

$R^1$ and $R^2$ can be taken together with the carbon atoms in the 4 and 5 position of the imidazole ring to represent a carbocyclic five- or six-membered aromatic or partially hydrogenated ring which may be substituted by $R^8$ or $R^9$;

$R^4$ and $R^5$ independently are H, $C_6H_5$ or alkyl of 1 to 9 carbon atoms;

$R^6$ is alkyl, cycloalkyl or hydroxyalkyl of 1 to 20 carbon atoms, H, alkali metal if X is —COO—, 1-phenethyl or

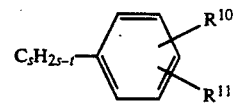

$R^7$ is H, OH if X is —$CONR^7$ or alkyl of 1 to 4 carbon atoms;

$R^8$, $R^9$, $R^{10}$ and $R^{11}$ are independently H, Cl, F, Br, $NO_2$, $CH_3CONH$, OH, alkyl of 1 to 3 carbon atoms, $CF_3$ or alkoxy of 1 to 3 carbons or $R^8$ and $R^9$ or $R^{10}$ and $R^{11}$ taken together represent methylenedioxy;

X is a bond, O, OC(=O)O, C(=O)O, $CONR^7$, OC(=O) or OC(=O)$NR^7$;

m and n taken together represent a whole number from to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

Durant et al., U.S. Pat. 4,228,291, issued Oct. 14, 1980, teaches compounds of the formula:

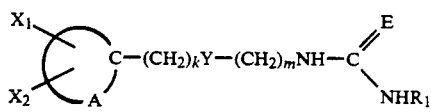

wherein

A together with the carbon atom form an unsaturated heterocyclic nucleus which may be an imidazole, pyrazole, pyrimidine, pyrazine, pyridazine, thiazole, isothiazole, oxazole, isoxazole, triazole, thiadiazole, benzimidazole or 5,6,7,8-tetrahydro-imidazol[1,5-a]pyridine ring;

$X_1$ is H, lower alkyl, hydroxyl, trifluoromethyl, benzyl, halogen, amino or

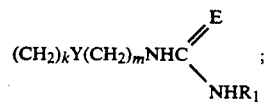

$X_2$ is H or when $X_1$ is lower alkyl, lower alkyl or halogen;

k is 0 to 2;

m is 2 or 3, provided that the sum of k and m is 3 or 4;

Y is O, S or NH;

E is $NR^2$;

$R^1$ is H, lower alkyl or di-lower alkyl amino-lower alkyl; and $R^2$ is H, nitro or cyano.

The compounds are said to be antihistamines of the $H_2$ receptor blocking type, as well as having anti-inflammatory activity.

White, U.S. Pat. 4,413,130, Nov. 1, 1983, discloses histamine $H_2$ receptor antagonists of the formula:

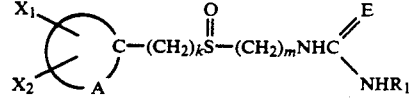

wherein:
A together with the carbon atom form an unsaturated heterocyclic nucleus which may be an imidazole, pyridine, thiazole, isothiazole, oxazole, isoxazole, pyrazole, triazole, thiadiazole, pyrimidine, pyrazine or pyridazine;
$X_1$ and $X_2$ may be H, lower alkyl, trifluoromethyl, hydroxyl, halogen, amino or $X_1$ and $X_2$ and at least two of the atoms comprising A may form a further ring;
k is 0 to 2;
m is 2 or 3, provided that the sum of k and m is 3 or 4;
E is O, S or $NR^2$;
$R^1$ is H, lower alkyl, acyl or dialkylaminoalkyl; and
$R^2$ is H, $NO_2$, CN, alkanesulfonyl or arenesulfonyl.

There are no known literature references disclosing the compounds of this invention, their use as ACAT inhibitors or their use to lower cholesterol or in the treatment of atherosclerosis.

The compounds of this invention are very potent ACAT inhibitors, and thus are expected to be useful in pharmaceutical formulations for the treatment of atherosclerosis. This invention should not be construed as limited to any particular antihypercholesterolemic mechanism of action.

SUMMARY OF THE INVENTION

The present invention provides novel compounds of Formula (I), processes for their preparation, pharmaceutical compositions containing such fused-ring heterocycles, and therapeutic methods for their use as antihypercholesterolemic agents.

This invention provides compounds of Formula (I):

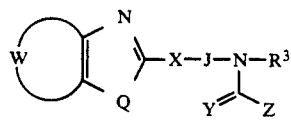

wherein
W is:

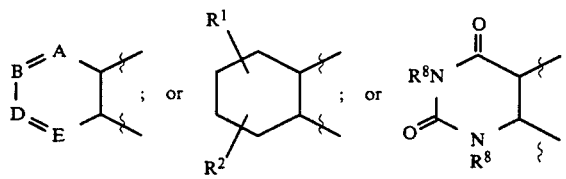

A, B, D, and E are selected independently from CRI or N with no more than two nitrogens per ring;
Q is NH, $NCH_3$, O or S;
X is $S(O)r$, O, $NR^5$ or $CH_2$;
J is $C_2$-$C_{10}$ alkyl, $C_3$-$C_{10}$ branched alkyl, $C_3$-$C_{10}$ alkenyl or $C_3$-$C_{10}$ alkynyl;
Y is O, S, $H_2$ or NH;
Z is $NHR^4$, $OR^4$ or $R^4$;
$R^1$ and $R^2$ are selected independently from H, Br, Cl, F, $CF_3$, CN, $NO_2$, $CH_3S(O)r$, $C_1$-$C_8$ alkyl or alkoxy, $C_3$-$C_8$ branched alkyl, $C_1$-$C_4$ carboalkoxy, $NR^6R^7$ or $NR^6COR^7$;
$R^3$ is $C_1$-$C_8$ alkyl, $C_3$-$C_8$ branched alkyl, $C_3$-$C_7$ cycloalkyl, $C_3$-$C_8$ alkenyl or alkynyl, $C_7$-$C_{14}$ araalkyl where the aryl group is optionally substituted with 1 to 3 groups selected from $C_1$-$C_4$ alkyl or alkoxy, F, Br, Cl, OH, CN, $CO_2H$, $CF_3$, $C_1$-$C_4$ carboalkoxy, $NR^6R^7$ or $NR^6COR^7$; phenyl optionally substituted with 1 to 3 groups selected from $C_1$-$C_4$ alkyl or alkoxy, F, Br, Cl, OH, CN, $CO_2H$, $CF_3$, $C_1$-$C_4$ carboalkoxy, $NR^6R^7$ or $NR^6COR^7$; benzyl optionally substituted with 1 to 3 groups selected from $C_1$-$C_4$ alkyl or alkoxy, F, Br, Cl, OH, CN, $CO_2H$, $CF_3$, $C_1$-$C_4$ carboalkoxy, $NR^6R^7$ or $NR^6COR^7$; 2-, 3- or 4pyridinyl, pyrimidinyl; or biphenyl;
$R^4$ is $C_1$-$C_8$ alkyl, $C_3$-$C_8$ branched alkyl, $C_3$-$C_7$ cycloalkyl, $C_4$-$C_{10}$ cycloalkylalkyl, $C_3$-$C_6$ alkenyl or alkynyl, $C_1$-$C_3$ perfluoroalkyl, $C_7$-$C_{14}$ araalkyl where the aryl group is optionally substituted with 1 to 3 groups selected from $C_1$-$C_4$ alkyl or alkoxy, $C_3$-$C_8$ branched alkyl, F, Br, Cl, OH, CN, $CO_2H$, $CF_3$, $C_1$-$C_4$ carboalkoxy, $NR^6R^7$ or $NR^6COR^7$; phenyl optionally substituted with 1 to 3 groups selected from $C_1$-$C_4$ alkyl or alkoxy, $C_3$-$C_8$ carboalkoxy, $NR^6R^7$ or $NR^6COR^7$; benzyl optionally substituted with 1 to 3 groups selected from $C_1$-$C_4$ alkyl or alkoxy, $C_3$-$C_8$ branched alkyl, F, Br, Cl, OH, CN, $CO_2H$, $CF_3$, $C_1$-$C_4$ carboalkoxy, $NR^6R^7$ or $NR^6COR^7$; 2-, 3- or 4-pyridinyl, pyrimidinyl; or biphenyl;
$R^5$ is H, $C_1$-$C_6$ alkyl or benzyl;
$R^6$ and $R^7$ are selected independently from H or $C_1$-$C_4$ alkyl;
$R^8$ is H, $C_1$-$C_6$ alkyl or phenyl;
r is 0 to 2;
or a pharmaceutically acceptable salt thereof.

More preferred are compounds of Formula (I) wherein:
NH or $NCH_3$;
X is $S(O)r$;
J is $C_2$-$C_{10}$ alkyl or $C_4$-$C_9$ branched alkyl;
Y is O;
Z is $NHR^4$;
$R^1$ and $R^2$ are selected independently from H, $NO_2$, $C_1$-$C_8$ alkyl or alkoxy, $C_3$-$C_8$ branched alkyl, $C_1$-$C_4$ carboalkoxy, $NR^6R^7$ or $NR^6COR^7$;
$R^3$ is $C_1$-$C_8$ alkyl, $C_3$-$C_8$ branched alkyl, $C_3$-$C_7$ cycloalkyl, $C_7$-$C_{14}$ araalkyl where the aryl group is optionally substituted with 1 to 3 groups selected from $CH_3$, $CH_3O$, F, $NH_2$, $NO_2$, Br, Cl, OH, CN, $CO_2H$, $CF_3$ or di($C_1$-$C_4$)alkylamino; phenyl optionally substituted with 1 to 3 groups selected from $CH_3$, $CH_3O$, F, $NH_2$, $NO_2$, Br, Cl, OH, CN, $CO_2H$, $CF_3$ or di($C_1$-$C_4$)alkylamino; benzyl optionally substituted with 1 to 3 groups selected from $CH_3$, $CH_3O$, F, $NH_2$, $NO_2$, Br, Cl, OH, CN, $CO_2H$, $CF_3$ or di($C_1$-$C_4$)-alkylamino; 2-, 3- or 4- pyridinyl, pyrimidinyl; or biphenyl;
$R^5$ is H.

More specifically preferred because of biological activity are compounds of Formula (I) wherein:
X is $S(O)r$;
J is $C_2$-$C_{10}$ alkyl;
$R^1$ is selected from H, $CH_3$ or $NO_2$;
$R^2$ is H;
$R^3$ is $C_1$-$C_8$ alkyl, $C_3$-$C_8$ branched alkyl, $C_7$-$C_{14}$ araalkyl where the aryl group is optionally substituted with 1 to 3 groups selected from $CH_3$, $CH_3O$, F, $NH_2$, $NO_2$ or di($C_1$-$C_4$) alkylamino; phenyl optionally substituted with 1 to 3 groups selected from $CH_3$, $CH_3O$, F, $NH_2$, $NO_2$ or di($C_1$-$C_4$) alkylamino; benzyl optionally substituted with 1 to 3 groups selected from $CH_3$, $CH_3O$, F, $NH_2$, $NO_2$ or di($C_1$-$C_4$)alkylamino; 2-, 3- or 4-pyridinyl, pyrimidinyl; or biphenyl;

$R^4$ is $C_1$-$C_8$ alkyl, $C_3$-$C_8$ branched alkyl, $C_7$-$C_{14}$ araalkyl where the aryl group is optionally substituted with 1 to 3 groups selected from $C_1$-$C_4$ alkyl or alkoxy, F, $NH_2$, $NO_2$, $C_1$-$C_4$ carboalkoxy or di($C_1$-$C_4$) alkylamino; phenyl optionally substituted with 1 to 3 groups selected from $C_1$-$C_4$ alkyl or alkoxy, F, $NH_2$, $NO_2$, $C_1$-$C_4$ carboalkoxy or di($C_1$-$C_4$)alkylamino; benzyl optionally substituted with 1 to 3 groups selected from $C_1$-$C_4$ alkyl or alkoxy, F, $NH_2$, $NO_2$, $C_1$-$C_4$ carboalkoxy or di($C_1$-$C_4$)alkylamino; 2-, 3- or 4- pyridinyl, pyrimidinyl; or biphenyl.

Specifically preferred are:
N-[5-(1H-Benzimidazol-2-ylthio)pentyl]-N'-(2,4-difluorophenyl)-N-heptylurea
N'-(2,4-Difluorophenyl)-N-heptyl-N[5-(6-nitro-1H-benzimidazol-2-ylthio)pentyl]urea
N'-(2,4-Difluorophenyl)-N-heptyl-N-[5-(3H-imidazo[4,5-b]pyridin-2-ylthio)pentyl]urea
N'-(2,4-Difluorophenyl)-N-heptyl-N-[5-(1-methyl-1H-benzimidazol-2-ylthio)pentyl]urea
N'-(2,4-Difluorophenyl)-N-heptyl-N-[5-(4,5,6,7-tetrahydro-1H-benzimidazol-2-ylthio)pentyl]urea
N-Heptyl-N'-(1-methylethyl)-N-[5-(2,3,6,9-tetrahydro-1,3-dimethyl-2,6-dioxo-1H-purin-8-ylthio)pentyl]urea

DETAILED DESCRIPTION OF THE INVENTION

Synthesis

The novel compounds of Formula (I) may be prepared using the reactions and techniques described in this section. The reactions are performed in solvents appropriate to the reagents and materials employed and suitable for the transformation being effected. It is understood by those skilled in the art of organic synthesis that the functionality present on the heterocycle and other portions of the molecule must be compatible with the reagents and reaction conditions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternative methods to those described must then be used.

The compounds of Formula (I) wherein X is O, S or NH can be prepared by the route shown in Scheme 1.

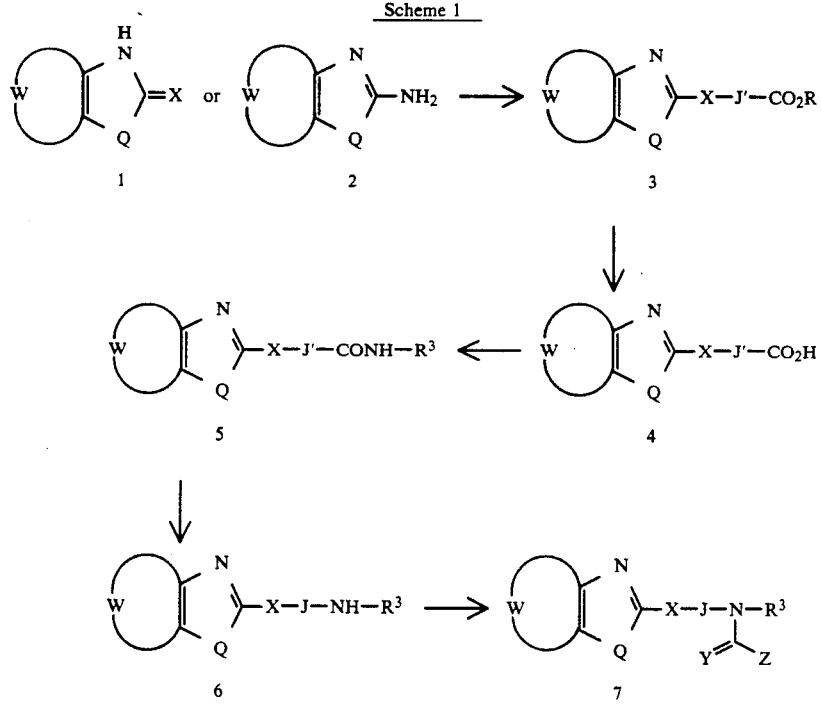

The compounds of Formula (1) wherein X is S or O, and Formula (2), Scheme 1, are available from commercial sources or can be prepared by methods which are well known in the chemical literature.

Alternately, the compounds of Formula (1) and (2) where W is a phenylene, pyridine or pyrimidine of the structure

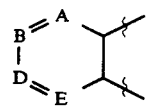

and Q is NH or $NCH_3$ Scheme 2, can be synthesized from the corresponding phenylenediamines, 4,5-diaminopyridines or 4,5-diaminopyrimidines of Formula (8) and urea to give compounds of Formula (9) where X is O, or thiourea or carbon disulfide or ammonium thiocyanate to give compounds of Formula (9) where X is S, or cyanogenbromide to give compounds of Formula (10), in a suitable solvent such as pyridine, N,N-dimethylformamide or 1-propanol.

Scheme 2

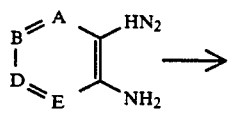

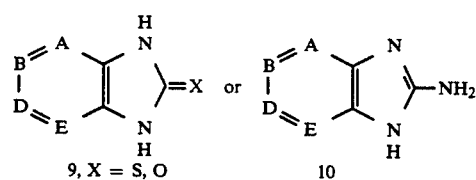

Similarly, the compounds of Formula (1) where W is a phenylene, pyridine or pyrimidine of the structure

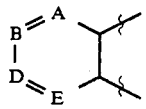

and Q is S, Scheme 3, can be synthesized from the corresponding o-aminothiophenols or 5-amino-4-mercaptopyrimidines of Formula (11) and phosgene to give compounds of Formula (12) where X is O, or carbon disulfide to give compounds of Formula (12) where X is S, in a suitable solvent such as toluene or tetrahydrofuran.

Scheme 3

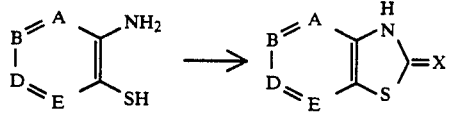

As shown in Scheme 4, the corresponding compounds of Formula (2) can be synthesized from the corresponding o-phenylthiocarbamides of Formula (13) and bromine in a solvent such as methylene chloride to give compounds of Formula (14).

Scheme 4

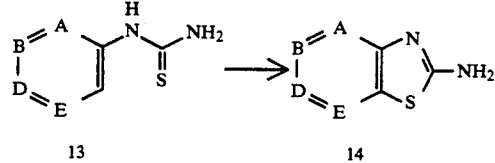

Similarly, the compounds of Formula (1) where W is a phenylene, pyridine or pyrimidine of the structure

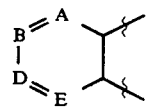

and Q is O, Scheme 5, can be synthesized from the corresponding o-aminophenols of Formula (15) and phosgene to give compounds of Formula (16) where X is O, or carbon disulfide to give compounds of Formula (16) where X is S, in a suitable solvent such as toluene or tetrahydrofuran.

Scheme 5

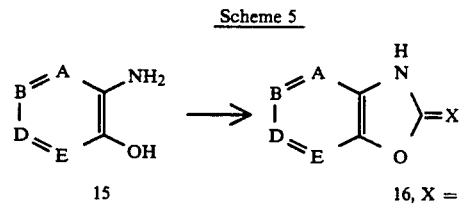

As shown in Scheme 6, the corresponding compounds of Formula (2) can be synthesized from the corresponding o-hydroxyphenylthiocarbamides of Formula (17) and mercuric oxide in a solvent such as methylene chloride to give compounds of Formula (18).

Scheme 6

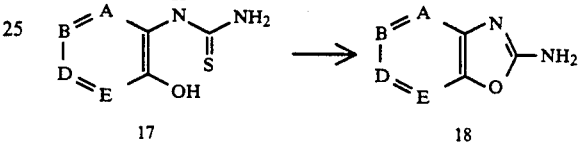

The compounds of Formula (1) and (2) where W is a pyrazine of the structure

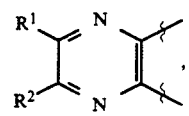

Scheme 7, can be synthesized by the condensation reaction of the appropriately substituted 1,2-dicarbonyl compounds of Formula (19) and appropriately substituted 1,2-diamines of Formula (20) in an azeotropic mixture of a suitable solvent such as toluene to give compounds of Formula (21) and (22).

Scheme 7

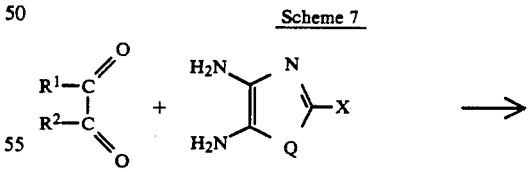

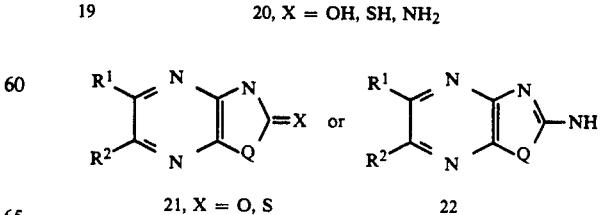

The compounds of Formula (1) and (2) where W is a pyridazine such as

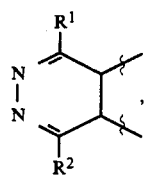

Scheme 8, can be synthesized from the corresponding 1,4-dicarbonyl compounds of Formula (23) and hydrazine in a suitable solvent such as ethanol to give compounds of Formula (24) and (25).

Scheme 8

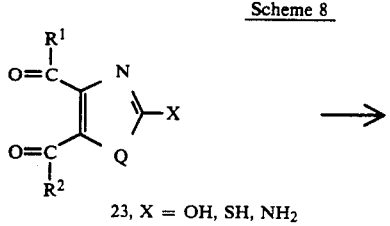

23, X = OH, SH, NH$_2$

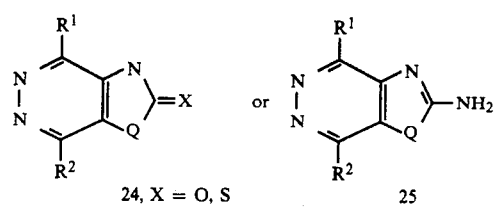

24, X = O, S          25

Similarly, the compounds of Formula (1) and (2) where W is a pyridazine such as

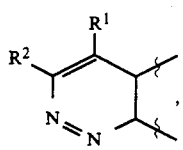

Scheme 9, can be synthesized from the corresponding 1,4-dicarbonyl compounds of Formula (26) and hydrazine in a suitable solvent such as ethanol to give compounds of Formula (27) and (28).

Scheme 9

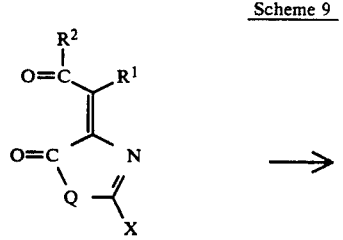

26, X = OH, SH, NH$_2$

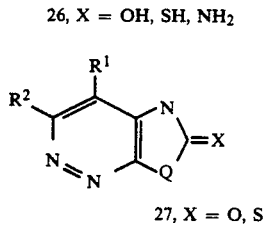

27, X = O, S          28

The compounds of Formula (1) and (2) where W is

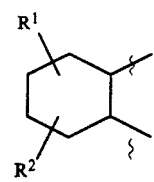

and Q is NH, Scheme 10, can be synthesized from the corresponding 2-ketocyclohexanols of Formula (29) and urea to give compounds of Formula (30) where X is O, or thiourea to give compounds of Formula (30) where X is S, or ammonia to give compounds of Formula (31), in a suitable solvent such as hexanol.

Scheme 10

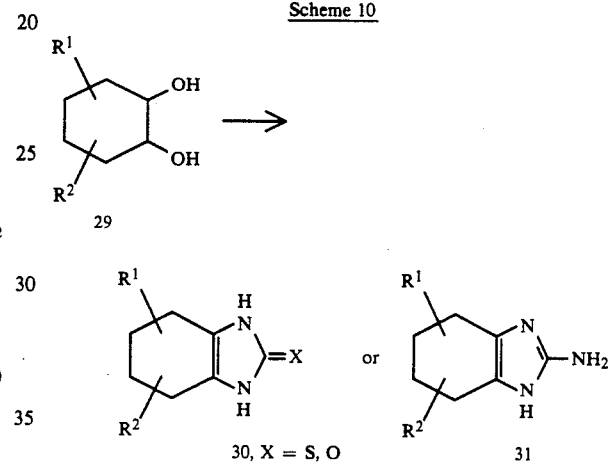

30, X = S, O          31

The compounds of Formula (1) and (2) where W is

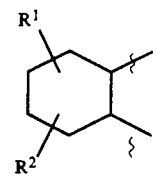

and Q is S, Scheme 11, can be synthesized from the corresponding 2-chlorocyclohexanones of Formula (32) and ammonium thiocarbamate to give compounds of Formula (33) where X is O, ammonium dithiocarbamate to give compounds of Formula (33) where X is S, or thiourea to give compounds of Formula (34), in a suitable solvent such as hexanol.

Scheme 11

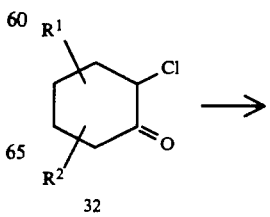

32

Scheme 11

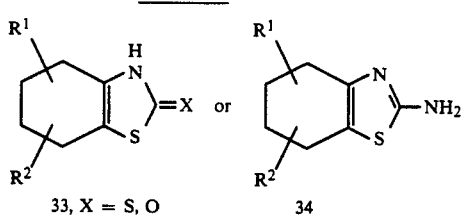

33, X = S, O        34

The compounds of Formula (1) and (2) where W is

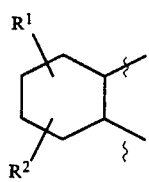

and Q is O, Scheme 12, can be synthesized from the corresponding 2-bromocyclohexanones of Formula (35) and formamide to give compounds of Formula (36) where X is O, thioamide to give compounds of Formula (36) where X is S, or urea to give compounds of Formula (37), in a suitable solvent such as hexanol.

Scheme 12

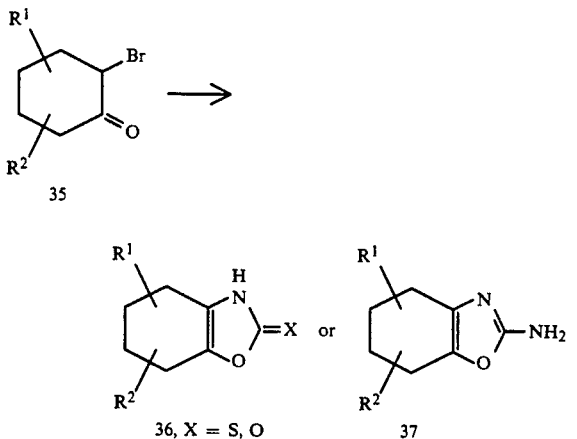

36, X = S, O        37

The compounds of Formula (1) and (2) where W is

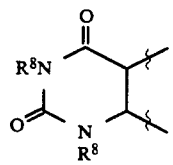

and Q is NH, Scheme 13, can be synthesized from the corresponding 5,6-diaminouracils of Formula (38) and urea to give compounds of Formula (39) where X is O, thiourea or carbon disulphide to give compounds of Formula (39) where X is S, or formamide to give compounds of Formula (40), in a suitable solvent such as pyridine or N,N-dimethylformamide or hexanol.

Scheme 13

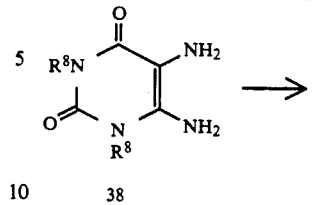

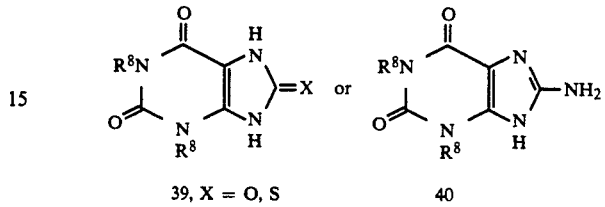

39, X = O, S        40

The compounds of Formula (41), Scheme 14, can be prepared from the corresponding compounds of Formula (42), *Org. Syn. Coll.*, Vol. II, 231, by reaction with Lawesson's reagent or diphosphorus pentasulfide in a suitable solvent such as toluene.

Scheme 14

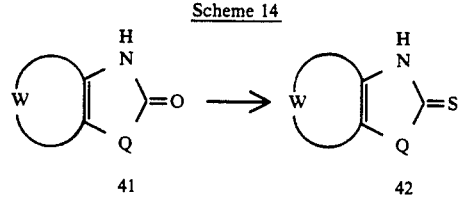

41        42

The esters of Formula (3) wherein X is O or S can be prepared by converting the requisite compounds of Formula (1) where X is O or compounds of Formula (1) where X is S, into the corresponding alkali metal salt by addition of a base such as sodium hydride, and the salt is alkylated with an appropriate compound of the formula M-(J')$CO_2$R, wherein R is $CH_3$ or $C_2H_5$, M is a L halogen or a tosylate group, and J' is a moiety having one less methylene group than J, in a polar solvent such as N,N-dimethylformamide. Alternatively, the esters of Formula (3) wherein X is S may be prepared by direct alkylation of the requisite compounds of Formula (1) with the appropriate compounds of the formula M-(J')$CO_2$R, without the addition of a suitable base, in a polar solvent such as N,N-dimethylformamide at a temperature from ambient temperature to the reflux temperature of the solvent. The esters of Formula (3) wherein X is NH can be prepared by the reaction of the requisite compounds of Formula (2) with the appropriate compounds of the formula M-(J')$CO_2$R wherein R, M, and J' are as defined above, in a suitable solvent such as N,N-dimethylformamide. Compounds of Formula (2) wherein Q is NH are preferentially alkylated at a ring nitrogen atom. Therefore, in order to prepare compounds of Formula (I) wherein X is NH and Q is NH, it is usually necessary to protect the ring nitrogen atom. The protecting group is preferably stable under basic conditions and easily removed under acidic conditions, e.g., a silyl or trityl group. The protected compounds of Formula (2) can then be used to prepare esters of Formula (3) wherein Q is N containing a protecting group. The protecting group can be removed at any suitable stage in the synthetic sequence for the preparation of the compounds of Formula (I) wherein X is NH and Q is NH.

The esters of Formula (3) are hydrolyzed to the corresponding carboxylic acids of Formula (4) by methods which are well known in the chemical literature. For example, the hydrolysis can be accomplished by reaction with an alkali metal hydroxide in aqueous or organic solvents such as water, alcohols, ethers or mixtures thereof, followed by acidification with a mineral acid. The methods used to prepare compounds of Formula (4) are substantially similar to the methods described in U.S. Pat. Nos. 4,654,358, 4,460,598 and 4,900,744 and European Patent Application EP-A-372,445, published on Jun. 13, 1990, the teaching of which is incorporated by reference.

The amides of Formula (5) are prepared by coupling the carboxylic acids of Formula (4) with a primary amine by amide bond forming reactions which are well known in the chemical literature. One method for amide bond formation is to use a coupling reagent which generates a reactive intermediate such as a mixed anhydride or active ester. Examples of such coupling agents are disubstituted carbodiimides, N,N'-carbonyldiimidazole, diphenylphosphoryl azide, and the like. For example, the coupling can be carried out with a disubstituted carbodiimide such as dicyclohexylcarbodiimide in an appropriate solvent such as methylene chloride, acetonitrile, toluene or N,N-dimethylformamide. Nucleophilic hydroxy compounds such as 1-hydroxy-1H-benzotriazole, which form highly active esters, may be added to catalyze the reaction.

There are several alternate approaches to the preparation of the amides of Formula (5). For example, the boron trifluoride etherate catalyzed reaction of the carboxylic acids of Formula (4) with a primary amine, with azeotropic removal of water, affords the amides of Formula (5). Another approach is to convert the carboxylic acids of Formula (4) to the corresponding acid chloride using thionyl chloride, oxalyl chloride or the like and then to react the acid chloride with a primary amine in the presence of a base such as triethylamine to afford the amides of Formula (5). Alternatively, the esters of Formula (3) can be directly converted to the amides of Formula (5) by ester aminolysis in the presence of strong alkali metal catalysts such as sodium amide, sodium hydride, sodium methoxide, Grignard reagents or butyllithium, or in the presence of milder catalysts such as 2-pyridone, boron tribromide or dimethylaluminum amides.

The amines of Formula (6) can be prepared by reduction of the corresponding amides of Formula (5) by a variety of methods well known to those skilled in the art. For example, reagents such as lithium aluminum hydride, diborane, sodium bis(2-methoxyethoxy)aluminum hydride (Red-Al®), and diisobutylaluminum hydride can be used to reduce an amide to an amine. Such reactions are typically conducted in an appropriate anhydrous aprotic solvent such as ether, toluene or tetrahydrofuran at a temperature from room temperature to the boiling point of the solvent for a period of 2-48 hours.

Alternatively, amines of Formula (6) wherein X is NH, can be prepared by the route shown in Scheme 15. The primary amines of Formula (44) can be prepared by reacting compounds of Formula (43) with an appropriately elaborated diamine under neat, thermal conditions or in an appropriate solvent such as N,N-dimethylformamide, toluene, acetonitrile or tetrahydrofuran, at or below the boiling point of the solvent.

Scheme 15

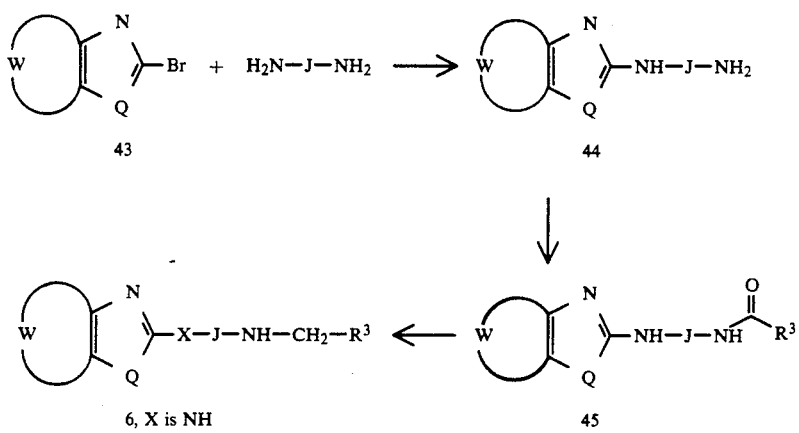

The secondary amines of Formula (6) wherein X is NH, can be prepared by direct alkylation of the primary amines of Formula (44) with an appropriately substituted alkyl halide. Or, the secondary amines (6) are prepared by acylation of the primary amines of Formula (44) with an acid chloride or activated carboxylic acid derivative to give the amide of Formula (45) and reduction of the amide (45) to the amines (6) by well known methods previously described.

The compounds of Formula (7) where Y is O and Z is $NR^4$, $OR^4$ or $R^4$, are prepared by the reaction of the secondary amines (6) with the requisite isocyanates, chloroformates, acid chlorides, activated urea or activated carboxylic acid derivatives in an appropriate solvent such as hexane, toluene, diethyl ether, diphenyl ether, methylene chloride or tetrahydrofuran at a temperature at or below the boiling point of the solvent.

The guanidines of Formula (7) wherein Y is NH and Z is $NR^4$, are prepared by the reaction of the secondary amines (6) with an appropriately substituted S-methyl carbamimidothioate salt (C.R. Rasmussen, F.J. Villani, et al., *Synthesis*, 460, 1988), in acetonitrile or dioxane at reflux.

The amines of Formula (7) wherein Y is $H_2$, are prepared by reaction of the corresponding ureas or amides of Formula (7) wherein Y is O, with a reducing agent such as lithium aluminum hydride or other such reagents in an appropriate anhydrous aprotic solvent such as hexane, toluene, diethylether or tetrahydrofuran at temperatures at or below the boiling point of the solvent.

As shown in Scheme 16, the thioureas of Formula (46) wherein X is S, O or NH and Z is $NHR^4$, can be prepared by the reaction of the secondary amines of Formula (6) with the requisite isothiocyanate. Alternatively, the thioureas or thioamides of Formula (46) where Z is $NHR^4$ or $R^4$, can be prepared from the ureas or amides of Formula (7) by the reaction with Lawesson's reagent or diphosphorus pentasulfide in an appropriate solvent such as toluene.

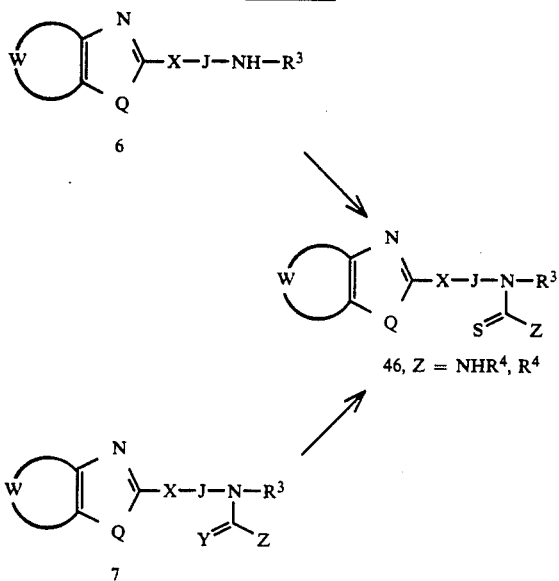

As shown in Scheme 17, the amides of Formula (5) can alternately be prepared by the alkylation of compounds of Formula (1) or (2) with compounds of the formula M-(J')CONHR$^3$ wherein M is a halogen or tosylate group, as described for compounds of Formula (3), Scheme 1.

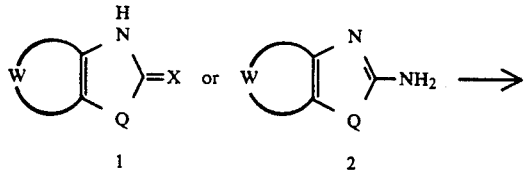

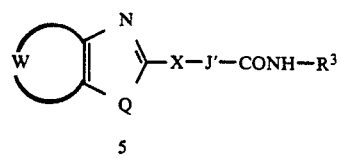

Alternatively, compounds of Formula (7) where X is O, S, or NH, can be prepared by the route shown in Scheme 18. The compounds of Formula (47) can be prepared from a lactone or an hydroxyalkylcarboxylic ester and an appropriate amine, neat or in an inert solvent such as N,N-dimethylformamide at ambient or elevated temperatures. The amines of Formula (48) are prepared by reduction of the corresponding amide of Formula (47) by a variety of well known methods, as previously described. The compounds of Formula (49) are prepared by the reaction of the secondary amines of Formula (47) with the requisite isocyanates, chloroformates, acid chlorides, activated ureas or activated carboxylic acid derivatives as described for the preparation of compounds of Formula (7), Scheme 1.

The compounds of Formula (50) can be prepared by conversion of the hydroxy group to a halogen moiety by a variety of well known methods. Examples of these methods are phosphorous tribromide, phosphorous oxychloride, thionyl chloride or triphenylphosphine and carbon tetrabromide. Alternately, compounds of Formula (50) where M is a tosylate or similar functionality, can be prepared from toluenesulfonyl chloride and triethylamine, in an appropriate aprotic solvent such as methylene chloride, tetrahydrofuran or toluene.

The compounds of Formula (7) can be prepared by converting the requisite compounds of Formula (1) where X is O or S, into the corresponding alkali metal salt by addition of a base such as sodium hydride, and alkylating with the compounds of Formula (50) in a polar aprotic solvent such as N,N-dimethylformamide at an appropriate temperature.

The compounds of Formula (7) wherein J is branched alkyl, can be prepared by a route analogous to that shown in Scheme 18. The requisite lactones with branching substituents can be prepared by functionalization of the parent unsubstituted lactones. Alternatively, branched cyclic a,w-diacid anhydrides can be reduced to the corresponding branched lactone using agents such as sodium borohydride. Synthesis of compounds of Formula (50) then proceeds exactly as described in the preceding paragraph, and alkylation of compounds of Formula (1) affords compounds of Formula (7), wherein J is branched alkyl.

Scheme 18

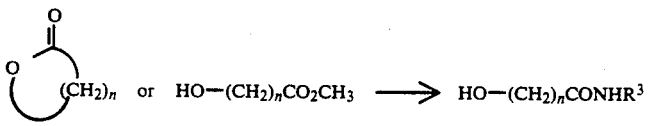

Scheme 18 -continued

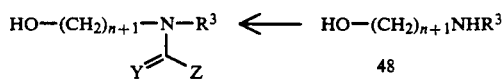

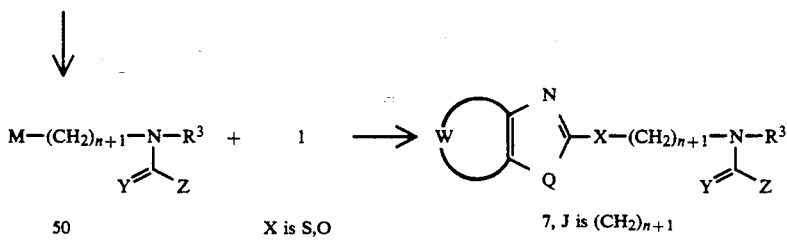

The compounds of Formula (7) wherein X is $CH_2$, are prepared by the route shown in Scheme 19. The compounds of Formula (52) are prepared by converting the requisite compounds of Formula (51) where Q is $NCH_3$ or N containing an appropriate protecting group, into the corresponding alkali metal salt, by addition of a base such as n-butyl lithium, and alkylating with an appropriate alkyl dihalide in a solvent such as tetrahydrofuran under an inert atmosphere and reduced temperatures. The compounds of Formula (53) are prepared by reacting the alkali metal salt of compounds of Formula (51) with the elaborated compounds of Formula (50) where M is Br under analogous conditions described above. The compounds of Formula (7) wherein X is $CH_2$ and Q is NH, are prepared by deprotecting compounds of Formula (54) where Q is N containing a protecting group such as trimethylsilylethylmethyl ether, for example, by removal with tetrabutylammonium fluoride in tetrahydrofuran at reflux.

Scheme 19

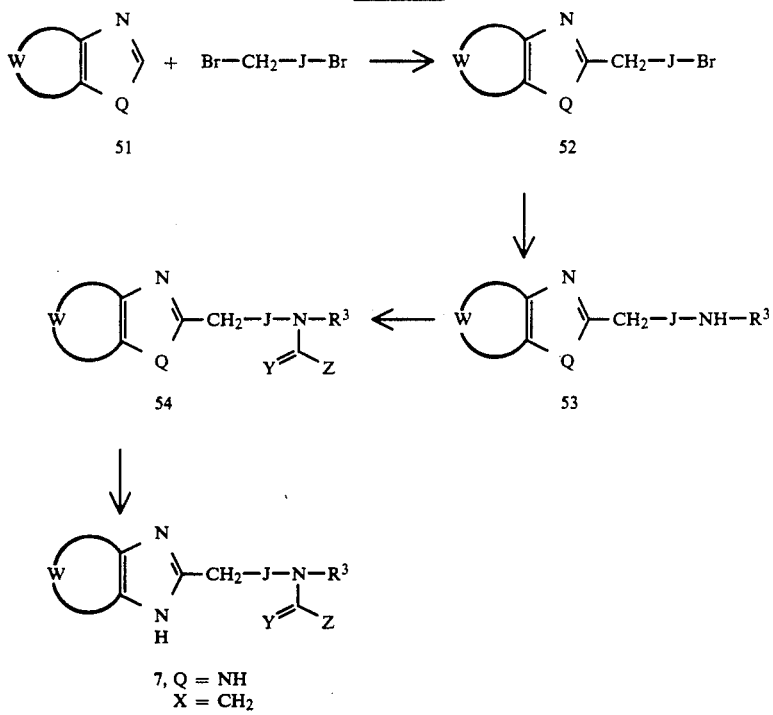

pared from compounds of Formula (52) by reaction with an appropriately substituted amine, in an inert solvent such as toluene, acetonitrile, tetrahydrofuran or N,N-dimethylformamide, at a temperature at or below the boiling point of the solvent. The compounds of Formula (54) are prepared by the reaction of the secondary amines of Formula (53) with the requisite isocyanate, chloroformate, acid chloride or other activated carboxylic acid derivative as previously described. Alternately, the compounds of Formula (54) can be prepared by reacting the alkali metal salt of compounds of Formula (51) with the elaborated compounds of Formula (50) where M is Br under analogous conditions described above. The compounds of Formula (7) wherein X is $CH_2$ and Q is NH, are prepared by deprotecting compounds of Formula (54) where Q is N containing a protecting group such as trimethylsilylethylmethyl ether, for example, by removal with tetrabutylammonium fluoride in tetrahydrofuran at reflux.

Likewise, compounds of Formula (7) wherein X is O, S, NH or $CH_2$ and Y is $H_2$, may be prepared by reacting compounds similar to compounds of Formula (52) with an appropriately functionalized secondary amine, $HN(CH_2Z)R^3$, in a solvent such as toluene, acetonitrile, tetrahydrofuran or N,N-dimethylformamide at a temperature at or below the boiling point of the solvent.

As shown in Scheme 20, the compounds of Formula (I) wherein X is S(O(,and r is 1 or 2, can be prepared by the oxidation of the compounds of Formula (55) by methods which are well known in the chemical literature. For example, the oxidation of (55) with one equivalent of a peracid such as m-chloroperoxybenzoic acid in a suitable solvent such as methylene chloride at a low temperature affords primarily the sulfoxides of Formula (56), and the oxidation of (55) with an oxidant such as potassium hydrogen persulfate or Oxone®, in a suitable solvent such as methanol affords the sulfones of Formula (57).

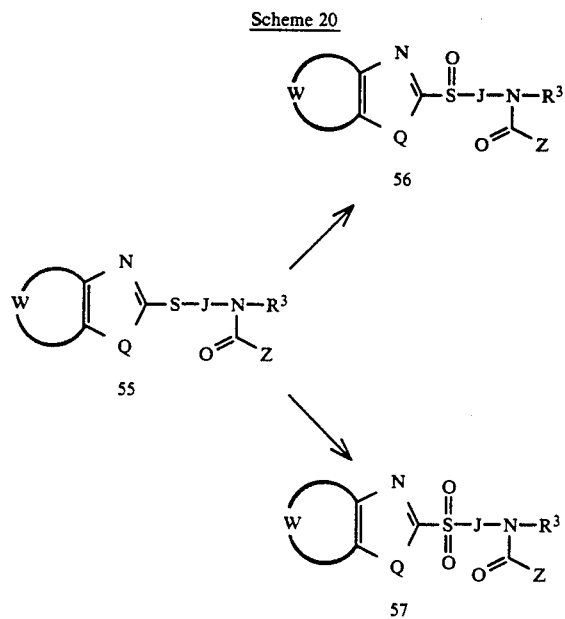

Scheme 20

The compounds of Formula (7) where Q is NCH₃, Scheme 21, can be prepared by direct alkylation of compounds of Formula (7) where Q is NH, in the presence or absence of a base such as potassium carbonate, pyridine, sodium hydride, triethylamine or potassium t-butoxide in an appropriate solvent such as N,N-dimethylformamide, glyme, tetrahydrofuran, pyridine or methylene chloride.

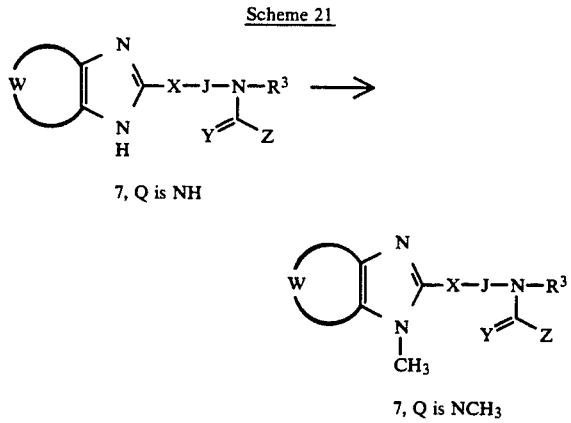

Scheme 21

Preparation of pharmaceutically suitable salts of Formula (I) can be carried out in accordance with well known techniques for forming salts. Physiologically acceptable salts include acid addition salts, e.g., hydrochloric, sulfuric, acetic, trifluoroacetic, succinic, citric, and benzene sulfonic acid salts.

The compounds of this invention and their preparation can be further understood by the following examples, which exemplify but do not constitute a limitation of the invention. In these examples, unless otherwise indicated, all temperatures are in degrees centigrade and parts and percentages are by weight.

EXAMPLE 1

Preparation of N'-(2,4-difluorophenyl)-N-heptyl-N-[5-(6-nitro-1H-benzimidazol-2-ylthio)pentyl]urea Part A. A solution of γ-valerolactone (25.0 g, 0.249 mol) in toluene (50 mL) and n-heptylamine (35.96 g, 0.312 mol) was heated to reflux for 18 hours under a nitrogen atmosphere. The reaction mixture was allowed to cool to ambient temperature, diluted with ethyl acetate (300 mL) and washed with 1 N aqueous HCl (50 mL), water and brine. The organic layer was dried over magnesium sulfate and then concentrated to give a white solid. The product was crystallized from ethyl ether:hexane to give N-heptyl-5-hydroxypentanamide (41.8 g, 0.194 mol) as white plates, mp 55°-56°. $^1$H NMR (CDCl₃) δ6.06 (bs,1H), 3.61 (t,2H,J=7.3 Hz), 3.24 (quartet,2H,J=8.4 Hz), 3.19 (bs,1H), 2.19 (t,2H,J=8.3 Hz), 1.80-1.23 (m,14H), 0.86 (t,3H,J=6.0 Hz).

Part B. To a solution of lithium aluminum hydride (6.7 g, 0.176 mol) in dry tetrahydrofuran (300 mL), a solution of N-heptyl-5-hydroxypentanamide (19.0 g, 0.088 mol) in dry tetrahydrofuran (100 mL) under a nitrogen atmosphere was added dropwise. The reaction mixture was heated to reflux for 18 hours, allowed to cool to room temperature and was poured slowly into a stirred mixture of 10% aqueous sodium sulfate (400 mL) and ice (200 mL). The resulting slurry was filtered through a bed of Celite ® and the filtrate was extracted with ethyl acetate (2×500 mL). The combined organic extracts were washed with water and brine, then dried over magnesium sulfate and concentrated to give a viscous yellow oil. The product was crystallized from hexane to give N-(5-hydroxypentyl)-N-heptylamine (15.2 g, 0.075 mol) as a white powder, mp 47°-48°. $^1$H NMR (CDCl₃) δ3.63 (t,2H,J=8.4 Hz), 2.63 (quartet,4H,J=8.3 Hz), 2.39 (bs,2H), 1.66-1.24 (m,16H), 0.91 (t,3H,J=6.6 Hz).

Part C. To a solution of N-(5-hydroxypentyl)-N-heptylamine (11.65 g, 0.0578 mol) in methylene chloride (75 mL) under a nitrogen atmosphere cooled to 0°, 2,4-difluorophenylisocyanate (8.97 g, 0.0578 mol) was added slowly. The reaction mixture was stirred for 1 hour, poured into 1 N aqueous HCl (200 mL) and was extracted with ethyl acetate (300 mL). The combined organic extracts were washed with water and brine, then dried over magnesium sulfate and concentrated to give N'-(2,4-difluorophenyl)-N-heptyl-N-5-hydroxypentylurea as a pale yellow oil (20.0 g, 0.056 mol). $^1$H NMR (CDCl₃) δ8.03 (m,1H), 6.88-6.59 (m,2H), 6.45 (bs,1H), 3.68 (t,2H,J=6.7 Hz).

Part D. To a solution of N'-(2,4-difluorophenyl)-N-heptyl-N-5-hydroxypentylurea (15.0 g, 0.042 mol) and carbon tetrabromide (16.75 g, 0.051 mol) in methylene chloride (350 mL) under a nitrogen atmosphere at ambient temperature, a solution of triphenylphosphine (13.24 g, 0.051 mol) in methylene chloride (100 mL) was added slowly. The reaction mixture was stirred for 3 hours and was concentrated in vacuo to give crude viscous oil. The product was purified by flash chromatography on silica gel (400 mL) eluting with hexane:ethyl acetate (90:10::v:v) to give N-(5-bromopentyl)-N'-(2,4-difluorophenyl)-N-heptylurea as a viscous colorless oil (17.5 g, 0.042 mol). $^1$H NMR (CDCl$_3$) δ8.14–8.00 (m,1H), 6.92–6.79 (m,2H), 6.35 (bs,1H), 3.49–3.25 (m,6H), 1.99–1.26 (m,16H), 0.92 (t,3H,J=6.7 Hz).

Part E. To a suspension of sodium hydride (0.04 g, 60% mineral oil dispersion, 0.001 mol; washed free of mineral oil with hexane) and sodium iodide (0.15 g; 0.0011 mol) in N,N-dimethylformamide (10 mL) under a nitrogen atmosphere, cooled to 0°, a solution of 6-nitrobenzimidazol-2-thione (0.975 g; 0.005 mol) in N,N-dimethylformamide (5 mL) was added slowly. The reaction mixture was stirred for 30 minutes and then a solution of N-(5-bromopentyl)-N'-(2,4-difluorophenyl)-N-heptylurea (0.42 g, 0.001 mol) in N,N-dimethylformamide (5 mL) was added. The reaction mixture was stirred for 1 hour and then allowed to warm to ambient temperature and stirred an additional 24 hours. The reaction mixture was poured into water (50 mL) and extracted with ethyl acetate (2×50 mL). The combined organic extracts were washed with water and brine, then dried over magnesium sulfate and concentrated to give a viscous oil. The product was purified by flash chromatography on silica gel eluting with hexane:ethyl acetate (75:25::v:v) to give the title compound (1.2 g, 0.00337 mol) as a solid, mp 120°–122°. $^1$H NMR (DMSO-d$_6$) δ13.25 (bs,1H), 8.27 (bs,1H), 8.05 (d,$^1$H,J=7.6 Hz), 7.91 (s,1H), 7.57 (d,1H,J=7.6 Hz), 7.4–7.3 (m,1H), 7.25–7.12 (m,1H), 7.0–6.8 (m,1H), 3.37–3.16 (m,6H), 1.85–1.72 (m,2H), 1.6–1.35 (m,6H), 1.27–1.1 (m,8H), 0.83 (t,3H,J=6.8 Hz).

EXAMPLE 2

Preparation of N'-(2,4-difluorophenyl-N-heptyl-N-[5(3H-imidazo[4,5-b]pyridin-2-ylthio)pentyl]urea Part A. A dry, nitrogen-purged flask was charged with 2,3-diaminopyridine (2.71 g, 24.8 mmol), pyridine (15 mL; freshly distilled from CaH$_2$) and carbon disulfide (9.0 mL). The flask was fitted with a condenser and a nitrogen line, the exit from which was scrubbed by bubbling into commercial bleach solution. The reaction mixture was heated to mild reflux for 2 hours, then cooled to 20° and stirred for 16 hours. The resulting pale tan solid was collected by filtration, and washed with water. A small second crop was obtained by pouring the filtrate into water (200 mL) and refiltering and washing the resulting precipitate. The two crops were combined, and recrystallized from water to give 2-mercaptoimidazo[4,5-b]-pyridine (3.01 g, 0.199 mol) as a solid, mp>250°. $^1$H NMR (DMSO-d$_6$) δ13.12 (br s,1H), 12.73 (br s,1H), 8.10 (d,1H,J=5.3 Hz), 7.47 (d,1H,J=7.5 Hz), 7.13 (dd,1H,J=7.5, 1.3 Hz).

Part B. A 100 mL flask was charged with 2-mercaptoimidazo[4,5-b]-pyridine (0.65 g, 0.0043 mol), sodium iodide (0.129 g, 0.00086 mol), and potassium carbonate (0.789 g, 0.00571 mol) in N,N-dimethylformamide (15 mL). A solution of N-(5-bromopentyl)-N-heptyl-N'-(2,4-difluorophenyl)urea (2.34 g, 0.00558 mol) in N,N-dimethylformamide (20 mL) was added and the mixture was heated to 60° C. under nitrogen atmosphere for 18 hours, then cooled and poured into ethyl acetate (100 mL). The ethyl acetate solution was washed with water (3×100 mL), dried over magnesium sulfate and concentrated. Purification by flash chromatography of the resulting residue afforded the product, which solidified upon standing overnight. The residue was recrystallized to afford the title compound (2.13 g, 0.0043 mol) as a viscous oil. $^1$H NMR (CDCl$_3$) δ8.27 (dd,1H,J=5.2, 1.4 Hz), 8.06–7.98 (m,1H), 7.91 (dd,1H,J=7.9, 1.3 Hz), 7.18 (dd,1H,J=7.9, 4.9 Hz), 6.84–6.76 (m,1H), 6.49 (d,1H,J=3.3 Hz), 3.41–3.24 (m,6H), 1.94–1.84 (m,2H), 1.74–1.51 (m,6H), 1.35–1.23 (m,8H), 0.88 (t,3H,J=6.6 Hz).

EXAMPLE 3

Preparation of N-5-(1H-benzimidazol-2-ylthio)pentyl]-N'-(2,4-difluorophenyl)-N-heptylurea Employing the method of Example 2, Part B, but using 2-mercaptobenzimidazole (0.15 g, 0.001 mol), the title compound (0.14 g, 0.00029 mol) was isolated as a viscous oil. $^1$H NMR (CDCl$_3$) δ10.2 (s,1H), 8.1–7.9 (m,1H), 7.7–7.5 (m,1H), 7.4–7.1 (m,4H), 6.9–6.7 (m,2H), 6.45 (s,1H), 3.4–3.2 (m,6H), 1.9–1.1 (m,16H), 0.9 (t,3H,J=6.3Hz).

EXAMPLE 4

Preparation of N'-(2,4-difluorophenyl)-N-heptyl-N-[5-(5-methyl-1H-benzimidazol-2-ylthio)pentyl]urea Employing the method of Example 2, Part B, but using 2-mercapto-5-methylbenzimidazole (0.16 g, 0.001 mol), the title compound (1.2 g, 0.00337 mol) was isolated as a yellow solid, mp 70°–72°. $^1$H NMR (CDCl$_3$) δ10.1 (bs, $^1$H), 8.1–7.9 (m, 1H), 7.6–7.4 (m, 1H), 7.1–7.0 (m, 2H), 6.9–6.8 (m, 2H), 6.5–6.4 (m,1H), 3.4–3.2 (m, 6H), 2.4 (s,3H), 1.9–1.2 (m, 16H), 0.9 (t, 3H, J=5.9Hz).

EXAMPLE 5

Preparation of N'-(2,4-difluorophenyl)-N-heptyl-N-[5-methyl-1H-benzimidazol-2-ylthio)pentyl]urea To a solution of potassium carbonate (0.14 g, 0.001 mol) in dry tetrahydrofuran (25 mL) was added, dropwise, a solution of N'-(2,4-difluorophenyl)-N-[5-(4,5-diphenyl-1H-imidazol-2-ylthio)pentyl]-N-heptylurea (0.49 g, 0.001 mol) in dry tetrahydrofuran (10 mL). The reaction mixture was then cooled to 0°. To this reaction mixture was added, dropwise, a solution of methyl iodide (0.09 mL, 0.21 g, 0.0015 mol) in dry tetrahydrofuran (10 mL). The reaction mixture was stirred for 1 hour at 0° and allowed to warm to ambient temperature and then stirred for an additional 16 hours. The reaction mixture was stirred for 8 hours at reflux and then at ambient temperature for an additional 72 hours. The reaction mixture was treated with another aliquot of methyl iodide (0.1 mL) and the reaction mixture was stirred at reflux for an additional 72 hours. The reaction mixture was again treated with a third aliquot of methyl iodide (0.1 mL) and the reaction mixture was stirred at reflux for an additional 72 hours. The reaction mixture was cooled and concentrated under vacuum. The residue was purified by flash chromatography eluting with hexane:ethyl acetate (70:30::v:v) to give the title compound (0.31 g, 0.00062 mol) as a yellow oil. $^1$H NMR (CDCl$_3$) δ8.1–8.0 (m,1H), 7.7–7.6 (m,1H), 7.3–7.1 (m,3H), 6.9–6.8 (m,2H), 6.5 (s,1H), 3.7 (s,3H), 3.4–3.2 (m,6H), 1.9–1.2 (m,16H), 0.9–0.8 (m,3H).

EXAMPLE 6

Preparation of N-5-(2-benzothiazolythio)pentyl -N'-2,4-difluorophenyl-N-heptylurea Employing the method of Example 2, Part B, but using 2-mercaptobenzthiazole (0.17 g, 0.001 mol), the title compound was isolated as a viscous oil (0.47 g, 0.00093 mol). $^1$H NMR (CDCl$_3$) δ8.1–8.0 (m,1H), 7.9–7.7 (m,2H), 7.5–7.3 (m,2H), 6.9–6.8 (m,2H), 6.5–6.4 (m, 1H), 3.4–3.2 (m,6H), 2.0–1.2 (m,16H), 1.0–0.8 (m,3H).

EXAMPLE 7

Preparation of N-heptyl-N-[5-(1H-imidazo-[4,5-b]pyridin-2-ylthio)-pentyl]-N'-(1-methylethyl)urea Employing the method of Example 2, Part B, but using N-(5-bromopentyl)-N-heptyl-N'-(1-methylethyl)urea (2.04 g, 0.00583 mol), the title compound (2.25 g, 0.00536 mol) was isolated as a solid, mp 101°–102°. $^1$H NMR (CDCl$_3$) δ8.27 (dd,1H,J=5.1, 1.3 Hz), 7.88 (dd,1H,J=8.1, 1.3 Hz), 7.14 (dd,1H,J=8.1, 5.1 Hz), 4.19 (d,1H,J=7.3 Hz), 3.97 (heptet,1H,J=6.6Hz), 3.34 (t,2H,J=7.1 Hz), 3.19 (t,2H,J=7.3 Hz), 3.09 (t,2H,J=8.2 Hz), 1.87–1.77 (m,2H), 1.58–1.38 (m,6H), 1.25–1.20 (m,8H), 1.11 (d,6H,J=6.6 Hz), 0.84 (t,3H,J=6.6 Hz).

EXAMPLE 8

Preparation of N-heptyl-N'-(1-methylethyl)-N-[5-(9H-purin-9-ylthio)pentyl]urea

Employing the method of Example 2, Part B, but using 8-mercaptopurine (0.73 g, 0.00316 mol) and N-(5-bromopentyl)-N-heptyl-N'-(1-methylethyl)urea (1.45 g, 0.00415 mol), the title compound (1.52 g, 0.00314 mol) was obtained as an amorphous solid. $^1$H NMR (CDCl$_3$) δ8.89 (br s,1H), 8.87 (br s,1H), 8.04 (s,1H), 4.22 (d,1H,J=6.9 Hz), 4.05 (m,1H, J=6.6 Hz), 3.34–3.26 (m,4H), 3.12 (t,2H,J=7.5 Hz), 1.92–1.82 (m,2H), 1.65–1.40 (m,6H), 1.30–1.20 (m,8H), 1.17 (d,6H,J=6.5 Hz), 0.88 (t,3H,J=6.2 Hz).

EXAMPLE 9

Preparation of N'-(2,4-difluorophenyl)-N-heptyl-N-[5-(9H-purin-9-ylthio)pentyl]urea Employing the method of Example 2, Part B, but using 8-mercaptopurine (0.73 g, 0.00316 mol), the title compound was obtained as an amorphous solid (0.80 g, 0.00163 mol). $^1$H NMR (CDCl$_3$) δ8.94 (br s,1H) 8.90 (br s,1H), 8.00 (br s,1H), 6.85–6.76 (m,2H), 6.49 (br d,1H,J=2.5 Hz), 3.46–3.26 (m,6H), 1.95–1.85 (m,2H), 1.74–1.60 (m,4H), 1.60–1.45 (m,2H), 1.42–1.20 (m,8H), 0.88 (t,3H,J=6.6 Hz).

EXAMPLE 10

Preparation of N'-(2,4-difluorophenyl)-N-[5-(6-ethoxy-2-benzothiazolyl)pentyl]-N-heptylurea Employing the method of Example 2, Part B, but using 6-ethoxy-2-mercaptobenzthiazole (0.21 g; 0.001 mol), the title compound was isolated as a viscous oil (0.53 g, 0.00099 mol). $^1$H NMR (CDCl$_3$) δ8.1–8.0 (m,1H), 7.7 (d,1H, J=8.1 Hz), 7.25–7.2 (m,1H), 7.1–7.0 (m,1H), 6.9–6.8 (m,2H), 6.5–6.4 (m, 1H), 4.1 (quartet, 2H, J=7.0 Hz), 3.4–3.2 (m,6H), 1.9–1.2 (m,20H), 0.95–0.8 (m,3H).

EXAMPLE 11

Preparation of N'-(2,4-difluorophenyl)-N-[5-(2-benzoxazolylthio)pentyl]-N-heptylurea Employing the method of Example 2, Part B, but using 2-mercaptobenzoxazole (0.15 g, 0.001 mol), the title compound was isolated as a viscous oil (0.26 g, 0.00053 mol). $^1$H NMR (CDCl$_3$) δ8.1–8.0 (m,1H), 7.6–7.55 (m,1H), 7.5–7.4 (m,1H), 7.3–7.2 (m,3H), 6.8–6.7 (m,2H), 6.5–6.4 (m,1H), 3.4–3.2 (m,6H), 1.9 (quintet,2H,J=7.3Hz), 1.8–1.2 (m,14H), 0.9 (t,3H,J=6.4Hz).

TABLE 1

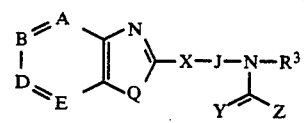

| EX | A | B | D | E | Q | X | J |
|---|---|---|---|---|---|---|---|
| 1 | CH | NO$_2$—C | CH | CH | NH | S | CH$_2$(CH$_2$)$_3$CH$_2$ |
| 2 | CH | CH | CH | N | NH | S | CH$_2$(CH$_2$)$_3$CH$_2$ |
| 3 | CH | CH | CH | CH | NH | S | CH$_2$(CH$_2$)$_3$CH$_2$ |
| 4 | CH | CH$_3$—C | CH | CH | NH | S | CH$_2$(CH$_2$)$_3$CH$_2$ |
| 5 | CH | CH | CH | CH | NCH$_3$ | S | CH$_2$(CH$_2$)$_3$CH$_2$ |
| 6 | CH | CH | CH | CH | S | S | CH$_2$(CH$_2$)$_3$CH$_2$ |
| 7 | CH | CH | CH | N | NH | S | CH$_2$(CH$_2$)$_3$CH$_2$ |
| 8 | CH | N | CH | N | NH | S | CH$_2$(CH$_2$)$_3$CH$_2$ |
| 9 | CH | N | CH | N | NH | S | CH$_2$(CH$_2$)$_3$CH$_2$ |
| 10 | CH | CH | CH$_3$CH$_2$O—C | CH | S | S | CH$_2$(CH$_2$)$_3$CH$_2$ |
| 11 | CH | CH | CH | CH | O | S | CH$_2$(CH$_2$)$_3$CH$_2$ |
| 12 | N | CH | CH | N | NH | S | CH$_2$CH(CH$_3$)(CH$_2$)$_3$ |
| 13 | N | CH | CH | N | NH | SO | (CH$_2$)$_3$CH(CH$_3$)CH$_2$ |
| 14 | N | CH | CH | N | NH | SO$_2$ | (CH$_2$)$_3$C(CH$_3$)$_2$CH$_2$ |
| 15 | N | CH | CH | N | NH | S | (CH$_2$)$_2$CH(C$_5$H$_{11}$)(CH$_2$)$_2$ |
| 16 | N | CH | CH | N | NCH$_3$ | S | CH(CH$_3$)(CH$_2$)$_4$ |
| 17 | N | CH | CH | N | NCH$_3$ | O | CH$_2$CH=CH(CH$_2$)$_2$ |
| 18 | N | CH | CH | N | NCH$_3$ | NCH$_3$ | (CH$_2$)$_3$CH=CH(CH$_2$)$_2$ |
| 19 | N | CH | CH | N | NCH$_3$ | CH$_2$ | CH$_2$C≡C(CH$_2$)$_2$ |
| 20 | N | CH | CH | N | O | SO | (CH$_2$)$_3$C≡C(CH$_2$)$_2$ |
| 21 | N | Cl—C | Cl—C | N | O | S | CH$_2$CH(CH$_3$)(CH$_2$)$_3$ |

TABLE 1-continued

| | | | | | | | | |
|---|---|---|---|---|---|---|---|---|
| 22 | N | CH₃CH₂CH—C | CH | N | NH | S | CH₂(CH₂)₅CH₂ |
| 23 | CH | N | N | CH | NH | S | CH₂CH(CH₃)(CH₂)₃ |
| 24 | CH | N | N | CH | NH | SO | (CH₂)₃CH(CH₃)CH₂ |
| 25 | CH | N | N | CH | NCH₃ | S | CH(CH₃)(CH₂)₄ |
| 26 | N | CH | CH | CH | NH | S | CH₂CH(CH₃)(CH₂)₃ |
| 27 | CH | N | CH | CH | NH | SO | (CH₂)₃CH(CH₃)CH₂ |
| 28 | N | CH | CH₃CH₂CH—C | CH | NH | S | CH₂(CH₂)₅CH₂ |
| 29 | CH | CH | CH | CH | NH | S | CH₂CH(CH₃)(CH₂)₃ |
| 30 | CH | CH | CH | CH | NH | SO | (CH₂)₃CH(CH₃)CH₂ |
| 31 | CH | CH | CH | CH | NH | SO₂ | (CH₂)₃C(CH₃)₂CH₂ |
| 32 | CH | CH | CH | CH | NH | S | (CH₂)₂CH(C₅H₁₁)(CH₂)₂ |
| 33 | CH | CH | CH | CH₃CH₂CH—C | NH | S | CH₂(CH₂)₅CH₂ |
| 34 | CH | CH | N | CH | NH | S | CH₂CH(CH₃)(CH₂)₃ |
| 35 | N | CH | N | CH | NH | SO | (CH₂)₃CH(CH₃)CH₂ |
| 36 | N | CH | N | CH | NH | SO₂ | (CH₂)₃C(CH₃)₂CH₂ |
| 37 | N | CH | N | CH | NH | S | (CH₂)₂CH(C₅H₁₁)(CH₂)₂ |
| 38 | N | CH | N | CH | NH | S | CH₂(CH₂)₅CH₂ |

| EX | R³ | Y | Z | Data (mp °C.) |
|---|---|---|---|---|
| 1 | (CH₂)₆CH₃ | O | NH-2,4-diF—C₆H₃ | 120–122 |
| 2 | (CH₂)₆CH₃ | O | NH-2,4-diF—C₆H₃ | oil$^{(a)}$ |
| 3 | (CH₂)₆CH₃ | O | NH-2,4-diF—C₆H₃ | oil$^{(b)}$ |
| 4 | (CH₂)₆CH₃ | O | NH-2,4-diF—C₆H₃ | 70–72 |
| 5 | (CH₂)₆CH₃ | O | NH-2,4-diF—C₆H₃ | oil$^{(c)}$ |
| 6 | (CH₂)₆CH₃ | O | NH-2,4-diF—C₆H₃ | oil$^{(d)}$ |
| 7 | (CH₂)₆CH₃ | O | NH—CH(CH₃)₂ | 101–102 |
| 8 | (CH₂)₆CH₃ | O | NH—CH(CH₃)₂ | gum$^{(e)}$ |
| 9 | (CH₂)₆CH₃ | O | NH-2,4-diF—C₆H₃ | gum$^{(f)}$ |
| 10 | (CH₂)₆CH₃ | O | NH-2,4-diF—C₆H₃ | oil$^{(g)}$ |
| 11 | (CH₂)₆CH₃ | O | NH-2,4-diF—C₆H₃ | oil$^{(h)}$ |
| 12 | CH₃ | O | NH-2,4-diOH—C₆H₃ | |
| 13 | CH₂CH(CH₃)₂ | S | NH-4-CN—C₆H₄ | |
| 14 | CH₂—C₆H₁₁ | H₂ | NH-2,4,6-triCF₃—C₆H₂ | |
| 15 | CH₂CH₂—C₆H₅ | NH | CH₂CH(CH₃)₂ | |
| 16 | 2,4-diF—C₆H₃ | O | CH₂—C₆H₁₁ | |
| 17 | CH₂CH=CH(CH₂)₂CH₃ | O | CH₂-2,6-diCH(CH₃)₂—C₆H₃ | |
| 18 | CH₂C≡C(CH₂)₂CH₃ | O | O—(CH₂)₇CH₃ | |
| 19 | CH₂-2,4-diOH—C₆H₃ | S | O—CH₂—C₆H₁₁ | |
| 20 | 4-CH₃O—C₆H₄ | S | O—CF₂CF₂CF₃ | |
| 21 | CH₂-4-pyridinyl | S | CH₂C≡C(CH₂)₂CH₃ | |
| 22 | 3-CN—C₆H₄ | NH | O-2,4-diCH₃—C₆H₃ | |
| 23 | CH₃ | O | NH-2,4-diOH—C₆H₃ | |
| 24 | CH₂CH(CH₃)₂ | S | NH-4-CN—C₆H₄ | |
| 25 | 2,4-diF—C₆H₃ | O | CH₂—C₆H₁₁ | |
| 26 | CH₃ | O | NH-2,4-diOH—C₆H₃ | |
| 27 | CH₂CH(CH₃)₂ | S | NH-4-CN—C₆H₄ | |
| 28 | 3-CN—C₆H₄ | S | O-2,4-diCH₃—C₆H₃ | |
| 29 | CH₃ | O | NH-2,4-diOH—C₆H₃ | |
| 30 | CH₂CH(CH₃)₂ | S | NH-4-CN—C₆H₄ | |
| 31 | CH₂—C₆H₁₁ | S | NH-2,4,6-triCF₃—C₆H₂ | |
| 32 | CH₂CH₂—C₆H₅ | O | CH₂CH(CH₃)₂ | |
| 33 | 3-CN—C₆H₄ | O | O-2,4-diCH₃—C₆H₃ | |
| 34 | CH₃ | O | NH-2,4-diOH—C₆H₃ | |
| 35 | CH₂CH(CH₃)₂ | S | NH-4-CN—C₆H₄ | |
| 36 | CH₂—C₆H₁₁ | O | NH-2,4,6-triCF₃—C₆H₂ | |
| 37 | CH₂CH₂—C₆H₅ | O | CH₂CH(CH₃)₂ | |
| 38 | 3-CN—C₆H₄ | O | O-2,4-diCH₃—C₆H₃ | |

Footnotes to Table 1:

$^{(a)1}$H NMR (CDCl₃)δ8.27(dd, 1H, J=5.2, 1.4Hz), 8.06–7.98(m, 1H), 7.91(dd, 1H, J=7.9, 1.3Hz), 7.18(dd, 1H, J=7.9, 4.9Hz), 6.84–6.67(m, 1H), 6.49(d, 1H, J=3.3Hz), 3.41–3.24(m, 6H), 1.94–1.84(m, 2H), 1.74–1.51(m, 6H), 1.35–1.23(m, 8H), 0.88(t, 3H, J=6.6Hz);

$^{(b)1}$H NMR (CDCl₃)δ10.2(s, 1H), 8.1–7.9(m, 1H), 7.7–7.5(m, 1H), 7.4–7.1(m, 4H), 6.9–6.7(m, 2H), 6.45(s, 1H), 3.4–3.2(m, 6H), 1.9–1.1(m, 16H), 0.9(t, 3H, J=6.3Hz);

$^{(c)1}$H NMR (CDCl₃)δ8.1–8.0(m, 1H), 7.7–7.6(m, 1H),7.3–7.1(m, 3H), 6.9–6.8(m, 2H), 6.5(s, 1H), 3.7(s, 3H), 3.4–3.2(m, 6H), 1.9–1.2(m, 16H), 0.9–0.8(m, 3H);

$^{(d)1}$H NMR (CDCl₃)δ8.1–8.0(m, 1H), 7.9–7.7(m, 2H), 7.5–7.3(m, 2H), 6.9–6.8(m, 2H), 6.5–6.4(m, 1H), 3.4–3.2(m, 6H), 2.0–1.2(m, 16H), 1.0–0.8(m, 3H);

$^{(e)1}$H NMR (CDCl₃)δ8.89(br s, 1H), 8.87(br s, 1H)8.04(s, 1H), 4.22(d, 1H, J=6.9Hz), 4.05(m, 1H, J=6.6Hz), 3.34–3.26(m, 4H), 3.12(t, 2H, J=7.5Hz), 1.92–1.82(m, 2H), 1.65–1.40(m, 6H), 1.30–1.20(m, 8H), 1.17(d, 6H, J=6.5Hz), 0.88(t, 3H, J=6.2Hz);

$^{(f)1}$H NMR (CDCl₃)δ8.94(br s, 1H), 8.90(br s, 1H), 8.00(br s, 1H), 6.85–6.76(m, 2H), 6.49(br d, 1H, J=2.5Hz), 3.46–3.26(m, 6H), 1.95–1.85(m, 2H), 1.74–1.60(m, 4H), 1.60–1.45(m, 2H), 1.42–1.20(m, 8H), 0.88(t, 3H, J=6.6Hz);

$^{(g)1}$H NMR (CDCl₃)δ8.1–8.0(m, 1H), 7.7(d, 1H, J=8.1Hz), 7.25–7.2(m, 1H), 7.1–7.0(m, 1H), 6.9–6.8(m, 2H), 6.5–6.4(m, 1H), 4.1(quartet, 2H, J=7.0Hz), 3.4–3.2(m, 6H), 1.9–1.2(m, 20H), 0.95–0.8(m, 3H);

$^{(h)1}$H NMR (CDCl₃)δ8.1–8.0(m, 1H), 7.6–7.55(m, 1H), 7.5–7.4(m, 1H), 7.3–7.2(m, 3H), 6.8–6.7(m, 2h), 6.5–6.4(m, 1H), 3.4–3.2(m, 6h), 1.9(quintet, 2H, J=7.3Hz), 1.8–1.2(m, 14H), 0.9(t, 3H, J=6.4Hz);

EXAMPLE 39

Preparation of N'-(2,4-difluorophenyl)-N-heptyl-N-[5-(4,5,6,7-tetrahydro-1H-benzimidazol-2-ylthio)pentyl]urea Part A. A solution of 2-hydroxycyclohexanol (2.28 g, 0.02 mol), thiourea (1.52 g, 0.02 mol) and hexanol (30 ml), equipped with a column of 4Å sieves and a condenser, was heated to 160° for five hours under a nitrogen atmosphere. The reaction mixture was allowed to cool to ambient temperature and was concentrated in vacuo to give a solid. The solid was triturated with ethyl ether (3×50 ml) to give 4,5,6,7-tetrahydrobenzimidazol-2-thione (0.6 g, 0.0039 mol) which was not purified but was taken on to the next step as a crude solid.

Part B. To a suspension of sodium hydride (0.099 g, 0.004 mol; washed free of the mineral oil with hexane) in N,N-dimethylformamide (15 ml) under a nitrogen atmosphere, cooled to 0°, 4,5,6,7-tetrahydrobenzimidazol-2-thione (0.50 g, 0.0033 mol) was added slowly. The reaction mixture was stirred for two hours and then a solution of N-(5-bromopentyl)-N'-(2,4-difluorophenyl)-N-heptyl urea (1.38 g, 0.0033 mol) in N,N-dimethylformamide (5 ml) was added. The reaction mixture was stirred at 0° for one hour, at ambient temperature for one hour, then was poured into water (50 ml) and extracted with ethyl acetate (2×50 ml). The combined organic extracts were washed with water and brine, then dried over magnesium sulfate and concentrated to give the crude product. The product was purified by flash chromatography on silica gel (250 ml) eluting with hexane: ethyl acetate (50:50::v:v) to give the title compound as a solid (0.30 g, 0.0006 mol), mp 98°-100°. $^1$H NMR (CDCl$_3$) δ10.0-9.4 (bs,1H), 8.05-7.87 (m,1H), 6.91-6.75 (m,2H), 6.5-6.41 (d,1H,J=3.75 Hz), 3.42-3.2 (m,4H), 2.96-2.85 (t,2H,J=6.0 Hz), 2.61-2.45 (m,4H), 1.81-1.22 (m,20H), 0.88 (t,3H,J=6.5 Hz).

mL) was treated with carbon disulfide (20 mL, 333 mmol) and then an aqueous solution of potassium hydroxide (50 mL, 8.0 g, 142 mmol). This mixture was heated to reflux for 20 hours under nitrogen atmosphere. After cooling to room temperature, the mixture was acidified by the addition of concentrated hydrochloric acid until the pH of the mixture was 5.5. The resulting precipitate was collected by filtration, washed with ethanol and dried under vacuum to afford 3,5-dimethyl-4,6-dioxo-8-mercapto-3,4,5,6-tetrahydro-8H-purine ethanol adduct (15.4 g, 59.7 mmol, 91%) as a solid, mp>250°. $^1$H NMR (DMSO-d$_6$) δ12.98 (br s,1H), 3.37 (s,3H), 3.35 (s,1H), 3.18 (s,3H).

Part B. 3,5-Dimethyl-4,6-dioxo-8-mercapto-3,4,5,6-tetrahydro-8H-purine ethanol adduct (2.00 g, 7.75 mmol) was dissolved in N,N-dimethylformamide (10 mL), and N-(5-bromopentyl)-N-heptyl-N'-isopropylurea (3.00 g, 8.94 mmol), sodium iodide (1.40 g, 9.33 mmol) and potassium carbonate (1.27 g, 9.19 mmol) were added. This mixture was heated to 90° for 18 hours, then cooled and poured into ice water (100 mL). The resulting mixture was extracted with ethyl acetate (100 mL), and the aqueous layer was neutralized to pH 7 with hydrochloric acid and reextracted with ethyl acetate (100 mL). The organic extracts were combined, then dried over magnesium sulfate and concentrated. The residue was purified by elution through a silica gel

TABLE 2

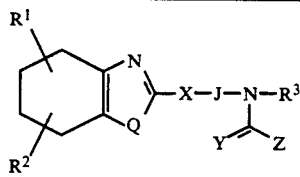

| EX# | R$^1$ | R$^2$ | Q | X | J | R$^3$ | Y | Z | Data (mp°C.) |
|---|---|---|---|---|---|---|---|---|---|
| 39 | H | H | NH | S | (CH$_2$)$_5$ | (CH$_2$)$_6$CH$_3$ | O | NH-2,4-diF—C$_6$H$_3$ | 98-100 |
| 40 | H | H | NH | S | CH$_2$CH(CH$_3$)(CH$_2$)$_3$ | CH$_3$ | O | NH-2,4-diOH—C$_6$H$_3$ | |
| 41 | H | H | NH | SO | (CH$_2$)$_3$CH(CH$_3$)CH$_2$ | CH$_2$CH(CH$_3$)$_2$ | S | NH-4-CN—C$_6$H$_4$ | |
| 42 | H | H | NH | SO$_2$ | (CH$_2$)$_3$C(CH$_3$)$_2$CH$_2$ | CH$_2$—C$_6$H$_{11}$ | H$_2$ | NH-2,4,6-triCF$_3$—C$_6$H$_2$ | |
| 43 | H | H | NH | S | (CH$_2$)$_2$CH(C$_5$H$_{11}$)(CH$_2$)$_2$ | CH$_2$CH$_2$—C$_6$H$_5$ | NH | CH$_2$CH(CH$_3$)$_2$ | |
| 44 | H | H | NH | S | CH$_2$CH=CH(CH$_2$)$_2$ | CH$_3$ | O | CH$_2$—C$_6$H$_5$ | |
| 45 | H | H | NH | S | (CH$_2$)$_3$CH=CH(CH$_2$)$_2$ | CH$_2$CH(CH$_3$)$_2$ | O | C$_6$H$_5$ | |
| 46 | H | H | NH | S | CH$_2$C≡C(CH$_2$)$_2$ | CH$_2$—C$_6$H$_{11}$ | S | CH$_2$—C$_6$H$_5$ | |
| 47 | H | H | NH | S | (CH$_2$)$_3$C≡C(CH$_2$)$_2$ | CH$_2$CH$_2$—C$_6$H$_5$ | S | O—CH(CH$_3$)$_2$ | |
| 48 | H | H | NH | S | CH$_2$(CH$_2$)$_6$CH$_2$ | 2,4,6-triCF$_3$—C$_6$H$_2$ | O | CH$_2$-2,4,6-triCH$_3$O—C$_6$H$_2$ | |
| 49 | H | H | NH | S | CH$_2$(CH$_2$)$_7$CH$_2$ | CH$_2$-4-CO$_2$H—C$_6$H$_4$ | O | NH-3-pyridinyl | |
| 50 | H | H | NH | S | CH$_2$(CH$_2$)$_8$CH$_2$ | 2,6-diCH$_3$O—C$_6$H$_3$ | O | CH$_2$-2-pyrimidinyl | |

EXAMPLE 51

Preparation of
N-heptyl-N'-(1-methylethyl)-N-[5-2,3,6,9-tetrahydro-1,3-dimethyl-2,6-dioxo-1H-purin-8-ylthio)pentyl]urea Part A. A slurry of 5,6-diamino-1,3-dimethyl uracil monohydrate (11.2 g, 65.8 mmol) in absolute ethanol (50 column using ethyl acetate:hexane:1:1 The resulting residue was recrystallized from hexane to afford the title compound (1.80 g, 3.74 mmol) as a viscous oil. $^1$H NMR (CDCl$_3$) δ12.87 (br s,1H), 4.01 (d,1H,J=6.2 Hz), 3.60 (s,3H), 3.45 (s,3H), 3.32-3.09 (m,6H), 1.86-1.76 (m,2H), 1.60-1.41 (m,8H), 1.35-1.25 (m,8H), 1.14 (d,6H,J=6.2 Hz), 0.88 (t,3H,J=6.4 Hz).

TABLE 3

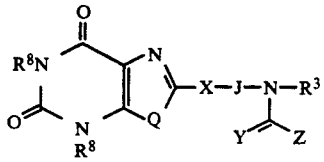

| EX# | R$^8$ | Q | X | J | R$^3$ | Y | Z | Data (mp°C.) |
|---|---|---|---|---|---|---|---|---|
| 51 | CH$_3$ | NH | S | (CH$_2$)$_5$ | (CH$_2$)$_6$CH$_3$ | O | NH—CH(CH$_3$)$_2$ | oil$^{(a)}$ |

TABLE 3-continued

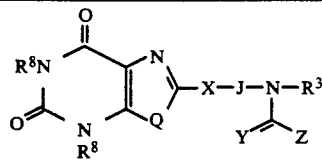

| EX# | R⁸ | Q | X | J | R³ | Y | Z | Data (mp°C.) |
|---|---|---|---|---|---|---|---|---|
| 52 | H | NH | S | CH₂CH(CH₃)(CH₂)₃ | CH₃ | O | NH-2,4-diOH—C₆H₃ | |
| 53 | CH₃CH₂ | NH | SO | (CH₂)₃CH(CH₃)CH₂ | CH₂CH(CH₃)₂ | S | NH-4-CN—C₆H₄ | |
| 54 | H | NH | SO₂ | (CH₂)₃C(CH₃)₂CH₂ | CH₂—C₆H₁₁ | H₂ | NH-2,4,6-triCF₃—C₆H₂ | |
| 55 | H | NH | S | (CH₂)₂CH(C₅H₁₁)(CH₂)₂ | CH₂CH₂—C₆H₅ | NH | CH₂CH(CH₃)₂ | |
| 56 | H | NCH₃ | S | CH(CH₃)(CH₂)₄ | 2,4-diF—C₆H₃ | O | CH₂—C₆H₁₁ | |
| 57 | H | NCH₃ | S | CH₂CH=CH(CH₂)₂ | CH₂CH=CH(CH₂)₂CH₃ | O | CH₂-2,6-diCH(CH₃)₂—C₆H₃ | |
| 58 | H | NCH₃ | S | (CH₂)₃CH=CH(CH₂)₂ | CH₂C≡C(CH₂)₂CH₃ | O | O—(CH₂)₇CH₃ | |
| 59 | H | NCH₃ | S | CH₂C≡C(CH₂)₂ | CH₂-2,4-diOH—C₆H₃ | S | O—CH₂—C₆H₁₁ | |
| 60 | H | NH | S | CH₂(CH₂)₇CH₂ | CH₂-3-pyridinyl | O | CH₂CH=CH(CH₂)₂CH₃ | |
| 61 | H | NH | S | CH₂(CH₂)₈CH₂ | CH₂-2-pyrimidinyl | S | O—C₆H₅ | |
| 62 | CH₃ | NH | S | CH₂CH(CH₃)(CH₂)₃ | CH₂-4-pyridinyl | S | CH₂C≡C(CH₂)₂CH₃ | |
| 63 | H | NH | S | CH₂(CH₂)₇CH₂ | CH₂-4-CO₂H—C₆H₄ | O | NH-3-pyridinyl | |
| 64 | H | NH | S | CH₂(CH₂)₈CH₂ | 2,6-diCH₃O—C₆H₃ | O | CH₂-2-pyrimidinyl | |

Footnotes to Table 3:
(a)¹H NMR (CDCl₃)δ12.87(br s, 1H), 4.01(d, 1H, J=6.2Hz), 3.60(s, 3H), 3.45(s, 3H), 3.32-3.09(m, 6H), 1.86-1.76(m, 2H), 1.60-1.41(m, 8H), 1.35-1.25(m, 8H), 1.14(d, 6H, J=6.2Hz), 0.88(t, 3H, J=6.4Hz).

Utility

The compounds of the present invention are inhibitors of the enzyme acyl-CoA: cholesterol acyltransferase and are thus effective in inhibiting esterification and transport of cholesterol across the intestinal wall. In addition, the compounds are useful in preventing the formation of cholesterol ester rich macrophages (foam cells) in the arterial wall through the inhibition of cholesterol ester formation. Foam cells are a source of the large quantity of cholesterol ester found in atheromatous lesions as opposed to the surrounding undiseased tissue. Thus inhibition of ACAT would decrease the accumulation and storage of cholesterol esters in the arterial wall and prevent or inhibit the formation of atheromatous lesions.

A. Assay of the Inhibition of Acyl-CoA: Cholesterol Acyltransferase (ACAT) in Hepatic Microsomes The ability of the compounds to inhibit ACAT, the enzyme responsible for the intracellular synthesis of cholesteryl esters, was tested as follows. Male Sprague Dawley rats weighing 150-300 g, were fed rat chow ad libitum. The animals were fasted for eighteen hours prior to being sacrificed by decapitation. The livers were perfused in situ with 50 mL of cold 0.25 M sucrose, excised, and homogenized in three volumes of 0.1 M phosphate buffer, pH 7.4, that contained 0.5 mM EDTA (ethylenediaminetetraacetic acid), 1.0 mM glutathione, 0.25 M sucrose and 20 μM leupeptin. Microsomes were obtained by differential centrifugation. The supernatant from an initial spin at 15,000×g for 15 minutes was centrifuged at 105,000×g for 1 hour to pelet the microsomes. The microsomes were suspended in 0.1 M phosphate buffer with 1 mM GSH, pH 7.4, reisolated by centrifugation, and stored at −70° C.

The control assay in a final volume of 200 μL consisted of 200 μg of microsomal protein, 77 μM ¹⁴C-oleoyl-CoA (10,000 dpm/nmol) in 0.1 M phosphate, pH 7.4 that contained 1 mM glutathione. Compounds were added in 5 μL of DMSO (dimethyl sulfoxide) and additional controls were run with DMSO only. All components, except the oleoyl-CoA, were preincubated for 15 min. at 7° C. prior to the initiation of the reaction by the addition of oleoyl-CoA. The assay was terminated after 10 min by the addition of 4 mL of chloroform:methanol (2:1::v:v). 30,000 dpm of ³H-cholesteryl oleate and 15 μg of unlabeled cholesteryl oleate and oleic acid were added as an internal standard and carriers, respectively. After allowing 20 min. for lipid extraction, 800 μL water was added to induce phase separation. The chloroform layer was transferred to another tube, dried under nitrogen and resuspended in 100 μL chloroform. Lipids were separated by thin layer chromatography using ITLC-SA thin layer plates (Gelman Sciences) and a solvent system of hexane:diethyl ether:acetic acid (170:30:1::v:v:v). The lipids were visualized by their interaction with iodine vapor and the cholesteryl ester spot was cut out and placed into a scintillation vial and counted. The specific activity of ACAT in the control incubation averaged 260 pmol/min/mg microsomal protein.

B. Assay of the Inhibition of Cholesterol Esterification in Mammalian Cells

The esterification of cholesterol was determined in the murine macrophage-like cell line J774.A1. Cells were seeded in 35 mm wells at a density of 300,000 cells per well in 2 mL of Dulbecco's Eagle Medium (DMEM) supplemented with 10% fetal bovine serum (FBS). Cells were incubated at 37° C. in an atmosphere of 5% CO₂ and humidity. After 24 hours the media was changed to 0.68 mL 10% FBS-DMEM containing 34 μg of acetylated human low density lipoprotein (ac-LDL) to increase the intracellular concentration of cholesterol and promote esterification. At 41 hours, various inhibitors were added to the cells in DMSO (10 μL/mL maximum). At 43 hours, the cells were pulsed with 0.1 mM ¹⁴C-oleic acid (10,000 dpm/nmol) complexed with BSA (bovine serum albumin) to follow cholesterol ester formation. The experiment was terminated at 45 hours by washing the monolayers 3 times with 3 mL of Tris-buffered saline at ° C. The lipids were extracted by incubating the monolayers with 1.5 mL of hexane: isopropanol (3:2::v:v) for 30 min. under gentle agitation. During this period, 10,000 dpm ³H-cholesteryl linoleate and 10 μg of cholesteryl oleate were added as an internal standard and carrier respectively. The organic solvent was removed and the cells were washed with an additional 1.0 mL of hexane: isopropanol which was combined with the original extract. The cells were allowed to dry overnight, digested with 1.5 mL of 0.2 N sodium hydroxide for 1 hour and an aliquot of the solubilized protein used for protein determination using the Lowry method. The organic extract was taken to dryness, resuspended in a solvent (3% diethyl ether, 97% hexane) for elution over a silica gel column and cholesterol esters extracted. Triglycerides were eluted with a solution of 25% diethyl ether in hexane. Scintillation cocktail was added to the eluted samples to determine the amount of radioactivity. The conversion of oleic acid to cholesteryl ester in the control averaged 0.54 mmol/hour/mg protein and was increased upon the addition of ac-LDL to about $10.69 \pm 0.69$ mmol/hour/mg protein.

Using the assay methods described above, the compounds of this invention are found to exhibit an activity of at least $IC_{50} < 55$ micromolar, thereby demonstrating and confirming the activity of these compounds as effective antihypercholesterolemic and/or antiatherosclerotic agents.

Dosage Forms:

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences*, 16th Edition, 1980.

In their therapeutic use as antihypercholesterolemic and/or antiatherosclerotic agents, the compounds of the invention are administered to the patient at dosage levels of 1 to 28 g per day. For a normal male adult human of approximately 70 kg of body weight, this translates into a dosage of 14 to 400 mg per kilogram body weight per day. The dosage administered will, of course, vary depending upon known factors such as the age, health, and weight of the recipient, nature and extent of symptoms, kind of concurrent treatment, frequency of treatment, and the effect desired. Useful pharmaceutical dosage forms for administration of the compounds of this invention can be illustrated as follows:

Tablets

Tablets are prepared by conventional procedures so that the dosage unit is 500 milligrams of active ingredient, 150 milligrams of lactose, 50 milligrams of cellulose and 10 milligrams of magnesium stearate.

Capsules

Capsules are prepared by conventional procedures so that the dosage unit is 500 milligrams of active ingredient, 100 milligrams of cellulose and 10 milligrams of magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendible Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogeneous paste.

The term "consisting essentially of" in the present disclosure is intended to have its customary meaning, namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited publications and applications may provide further useful information, however, these cited materials are hereby incorporated by reference.

What is claimed is:

1. A method of treating hypercholesterolemia or atherosclerosis in a mammal in need of such treatement comprising administering to the mammal a therapeutically effective amount of a compound of the formula (I):

[Structure I]

wherein
W is:

[Structure]

A, B, D, and E are each $CR^1$;
Q is NH, $NCH_3$;
X is $S(O)_r$, O, $NR^5$ or $CH_2$;
J is $C_2-C_{10}$ alkyl, $C_3-C_{10}$ branched alkyl, $C_3-C_{10}$ alkenyl or $C_3-C_{10}$ alkynyl;
Y is O, S, or NH;
Z is $NHR^4$, $OR^4$ or $R^4$;
$R^3$ is $C_1-C_8$ alkyl, $C_3-C_8$ branched alkyl, $C_3-C_7$ cycloalkyl, $C_3-C_8$ alkenyl or alkynyl, $C_7-C_{14}$ aralkyl where the aryl group is optionally substituted with 1 to 3 groups selected from $C_1-C_4$ alkyl or alkoxy, F, Br, Cl, OH, CN, $CO_2H$, $CF_3$, Carbo($C_{1-4}$)alkoxy, $NR^6R^7$ or $NR^6COR^7$; phenyl optionally substituted with 1 to 3 groups selected from $C_1-C_4$ alkyl or alkoxy, F, BR, Cl, OH, CN, $CO_2H$, $CF_3$, Carbo($C_1-C_4$)alkoxy, $NR^6R^7$ or $NR^6COR^7$; benzyl optionally substituted with 1 to 3 groups selected from $C_1-C_4$ alkyl or alkoxy, F, Br, Cl, OH, CN, $CO_2H$, $CF_3$, $C_1-C_4$ carboalkoxy, $NR^6R^7$ or $NR^6COR^7$; 2-, 3-, or 4-pyridinyl, pyrimidinyl; or biphenyl;

$R^4$ is $C_1-C_8$ branched alkyl, $C_3-C_7$ cycloalkyl, $C_4-C_{10}$ cycloalkylalkyl, $C_3-C_6$ alkenyl or alkynyl, $C_1-C_3$ perfluoroalkyl, $C_7-C_{14}$ aralkyl where the aryl group is optionally substituted with 1 to 3 groups selected from $C_1-C_4$ alkyl or alkoxy, $C_3-C_8$ branched alkyl, F, Br, Cl, OH, CN, $CO_2H$, $CF_3$, Carbo($C_1-C_4$)alkoxy, $NR^6R^7$ or $NR^6COR^7$; phenyl optionally substituted with 1 to 3 groups selected from $C_1-C_4$ alkyl or alkoxy, $C_3-C_8$ branched alkyl, F, Br, Cl, OH, CN, $CO_2H$, $CF_3$, Carbo($C_1-C_4$)alkoxy, $NR^6R^7$ or $NR^6COR^7$; benzyl optionally substituted with 1 to 3 groups selected from $C_1-C_4$ alkyl or alkoxy, $C_3-C_8$ branched alkyl, F, Br, Cl, OH, CN, $CO_2H$, $CF_3$, $C_1-C_4$ carboalkoxy, $NR^6R^7$ or $NR^6COR^7$; 2-, 3-, or 4-pyridinyl, pyrimidinyl; or biphenyl;

$R^5$ is H, $C_1-C_6$ alkyl or benzyl;
$R^6$ and $R^7$ are selected independently from H or $C_1-C_4$ alkyl;
r is 0 or 2;
or a pharmaceutically acceptable salt thereof.

2. The method of claim 1 wherein:
X is $S(O)_r$;
J is $C_2-C_{10}$ alkyl, $C_3-C_9$ branched alkyl;
Y is O;
Z is $NHR^4$;
$R^3$ is $C_1-C_8$ alkyl, $C_3-C_8$ branched alkyl, $C_3-C_7$ cycloalkyl, $C_7-C_{14}$ aralkyl where the aryl group is optionally substituted with 1 to 3 groups selected from $CH_3$, $CH_3O$, F, $NH_2$, Br, Cl, OH, CN, $CO_2H$, $CF_3$, or di($C_1-C_4$)alkylamino; phenyl optionally substituted with 1 to 3 groups selected from $CH_3$, $CH_3O$, F, $NH_2$, Br, Cl, OH, CN, $CO_2H$, $CF_3$, or di($C_1-C_4$)alkylamino; benzyl optionally substituted with 1 to 3 groups selected from $CH_3$, $CH_3O$, F, $NH_2$, Br, Cl, OH, CN, $CO_2H$, $CF_3$ or di($C_1-C_4$)alkylamino; 2-, 3-, or 4-pyridinyl, pyrimidinyl; or biphenyl; and
$R^5$ is H.

3. The method of claim 1 wherein:
X is $S(O)_r$;
J is $C_2-C_{10}$ alkyl;
$R^3$ is $C_1-C_8$ alkyl, $C_3-C_8$ branched alkyl, $C_7-C_{14}$ aralkyl where the aryl group is optionally substituted with 1 to 3 groups selected from $CH_3$, $CH_3O$, F, $NH_2$, or di($C_1-C_4$)alkylamino; phenyl optionally substituted with 1 to 3 groups selected from $CH_3$, $CH_3O$, F, $NH_2$, benzyl optionally substituted with 1 to 3 groups selected from $CH_3$, $CH_3O$, F, $NH_2$, 2-, 3-, or 4-pyridinyl, pyrimidinyl; or biphenyl;
$R^4$ is $C_1-C_8$ alkyl, $C_3-C_8$ branched alkyl, $C_7-C_{14}$ aralkyl where the aryl group is optionally substituted with 1 to 3 groups selected from $C_1-C_4$ alkyl or alkoxy, F, $NH_2$, phenyl optionally substituted with 1 to 3 groups selected from $C_1-C_4$ alkyl or alkoxy, F, $NH_2$, benzyl optionally substituted with 1 to 3 groups selected from $C_1-C_4$ alkyl or alkoxy, F, $NH_2$, 2-, 3- or 4-pyridinyl, pyrimidinyl; or biphenyl.

4. The method of claim 1 wherein the compound is N-[5-(1H-Benzimidazol-2-ylthio)pentyl]-N'-(2,4-difluorophenyl)-N-heptylurea.

5. The method of claim 1 wherein the compound is N'-(2,4-Difluorophenyl)-N-heptyl-N-[5-(5-methyl-1H-benzimidazol-2-ylthio)pentyl]urea.

6. The method of claim 1 wherein the compound is N'-(2,4-Difluorophenyl)-N-heptyl-N-[5-(6-nitro-1H-benzimidazol-2-ylthio)pentyl]urea.

7. The method of claim 1 wherein the compound is N'-(2,4-Difluorophenyl)-N-heptyl-N-[5-(1-methyl-1H-benzimidazol-2-ylthio)pentyl]urea.

8. The method of claim 1 wherein the compound is N'-(2,4-Difluorophenyl)-N-heptyl-N-[5-(4,5,6,7-tetrahydro-1H-benzimidazol-2-ylthio)pentyl]urea.

* * * * *